(12) United States Patent
Takaoka et al.

(10) Patent No.: US 8,717,571 B2
(45) Date of Patent: May 6, 2014

(54) OPTICAL MEASUREMENT APPARATUS AND OPTICAL MEASUREMENT SYSTEM

(71) Applicants: Olympus Corporation, Tokyo (JP); Olympus Medical Systems Corp., Tokyo (JP)

(72) Inventors: Hideyuki Takaoka, Hachioji (JP); Kazuhiro Gono, Sagamihara (JP); Takeshi Suga, Hino (JP)

(73) Assignees: Olympus Corporation, Tokyo (JP); Olympus Medical Systems Corporation, Tokyo (JP)

( * ) Notice: Subject to any disclaimer, the term of this patent is extended or adjusted under 35 U.S.C. 154(b) by 0 days.

(21) Appl. No.: 13/868,365

(22) Filed: Apr. 23, 2013

(65) Prior Publication Data

US 2013/0271768 A1    Oct. 17, 2013

Related U.S. Application Data

(63) Continuation of application No. PCT/JP2011/074569, filed on Oct. 25, 2011.

(60) Provisional application No. 61/408,160, filed on Oct. 29, 2010.

(51) Int. Cl.
*G01B 9/00* (2006.01)
*G01N 21/25* (2006.01)
*G01N 21/55* (2006.01)

(52) U.S. Cl.
USPC ............................ 356/445; 356/126; 356/413

(58) Field of Classification Search
USPC .................. 356/432–444, 445–458, 450–458
See application file for complete search history.

(56) References Cited

U.S. PATENT DOCUMENTS 4,862,258 A * 8/1989 Kidawara et al. ............... 348/70
6,231,503 B1 * 5/2001 Sugimoto et al. ............ 600/178
6,665,462 B2 * 12/2003 Wu et al. ......................... 385/18
6,819,826 B2 * 11/2004 Chang et al. .................... 385/18
7,236,658 B2 * 6/2007 Uesugi et al. ................... 385/18

FOREIGN PATENT DOCUMENTS

| JP | A-63-281116 | 11/1988 |
| JP | A-63-281117 | 11/1988 |
| JP | A-6-109981 | 4/1994 |
| JP | A-2002-291764 | 10/2002 |
| JP | A-2006-158716 | 6/2006 |

OTHER PUBLICATIONS

International Search Report issued in International Patent Application No. PCT/JP2011/074569 dated Jan. 31, 2012.

* cited by examiner

*Primary Examiner* — Kara E. Geisel
*Assistant Examiner* — Jarreas C Underwood
(74) *Attorney, Agent, or Firm* — Oliff PLC

(57) ABSTRACT

An optical measurement apparatus includes a connector where a base end portion of a measurement probe introduced into a subject is connected, a light source unit that emits illumination light irradiated from a leading end of the measurement probe, an optical measurement unit that measures reflection light and/or scattering light of the illumination light incident through the measurement probe, a first optical path that transmits the illumination light emitted by the light source unit to the optical measurement unit, a second optical path that transmits, to the measurement probe, the illumination light emitted by the light source unit and transmits, to the optical measurement unit, reflection light and/or scattering light of the illumination light incident through the measurement probe, and an optical path switching unit that switches an optical path for transmitting the illumination light into the first optical path or the second optical path.

9 Claims, 23 Drawing Sheets

OPTICAL MEASUREMENT APPARATUS AND OPTICAL MEASUREMENT SYSTEM

CROSS-REFERENCE TO RELATED APPLICATIONS

This application is a continuation of PCT international application Ser. No. PCT/JP2011/074569 filed on Oct. 25, 2011 which designates the United States, incorporated herein by reference, and which claims the benefit of priority from U.S. Provisional Patent Application No. 61/408,160, filed on Oct. 29, 2010, incorporated herein by reference.

BACKGROUND OF THE INVENTION

1. Field of the Invention

The present invention relates to an optical measurement apparatus and an optical measurement system for introducing a measurement probe into a subject, irradiating illumination light onto the measurement target, and estimating a property and a condition of the measurement target based on a measurement value of detection light reflected or scattered from tissue.

2. Description of the Related Art

In the related art, there is known an optical measurement system that irradiates illumination light onto a sample such as tissue and estimates a property and a condition of a sample based on a measurement value of detection light reflected or scattered from the sample. Such an optical measurement system includes an optical measurement apparatus having a light source that emits illumination light to the sample and a detection unit for detecting detection light from the sample and a measurement probe that is detachable to the optical measurement apparatus and is introduced into the subject.

However, in the optical measurement system described above, if abnormality occurs in the measurement value of the sample when the measurement probe is installed in the optical measurement apparatus, and the measurement for the sample is performed, it is necessary to specify an abnormal portion of the optical measurement system. For example, under a situation that abnormality occurs in the measurement value of the sample, it is necessary to specify whether or not abnormality occurs in the optical measurement apparatus or whether or not abnormality occurs in the measurement probe. In this regard, there is known a technique in which an optical sensor is provided in a base end portion or a leading end portion of the measurement probe, and information indicating that abnormality occurs in the measurement probe is output when the optical sensor is not able to detect the illumination light emitted from the light source or the detection light reflected from the sample (for example, refer to Japanese Laid-open Patent Publication No. 2002-291764 and Japanese Laid-open Patent Publication No. 2006-158716).

SUMMARY OF THE INVENTION

In accordance with some embodiments, an optical measurement apparatus and an optical measurement system are presented.

In some embodiments, an optical measurement apparatus includes: a connector where a base end portion of a measurement probe introduced into a subject is connected; a light source unit that emits illumination light irradiated from a leading end of the measurement probe; an optical measurement unit that measures reflection light and/or scattering light of the illumination light incident through the measurement probe; a first optical path that transmits the illumination light emitted by the light source unit to the optical measurement unit; a second optical path that transmits, to the measurement probe, the illumination light emitted by the light source unit and transmits, to the optical measurement unit, reflection light and/or scattering light of the illumination light incident through the measurement probe; and an optical path switching unit that switches an optical path for transmitting the illumination light into the first optical path or the second optical path.

In some embodiments, an optical measurement system includes the above described optical measurement apparatus, and the measurement probe that can be attached to or detached from the optical measurement apparatus.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
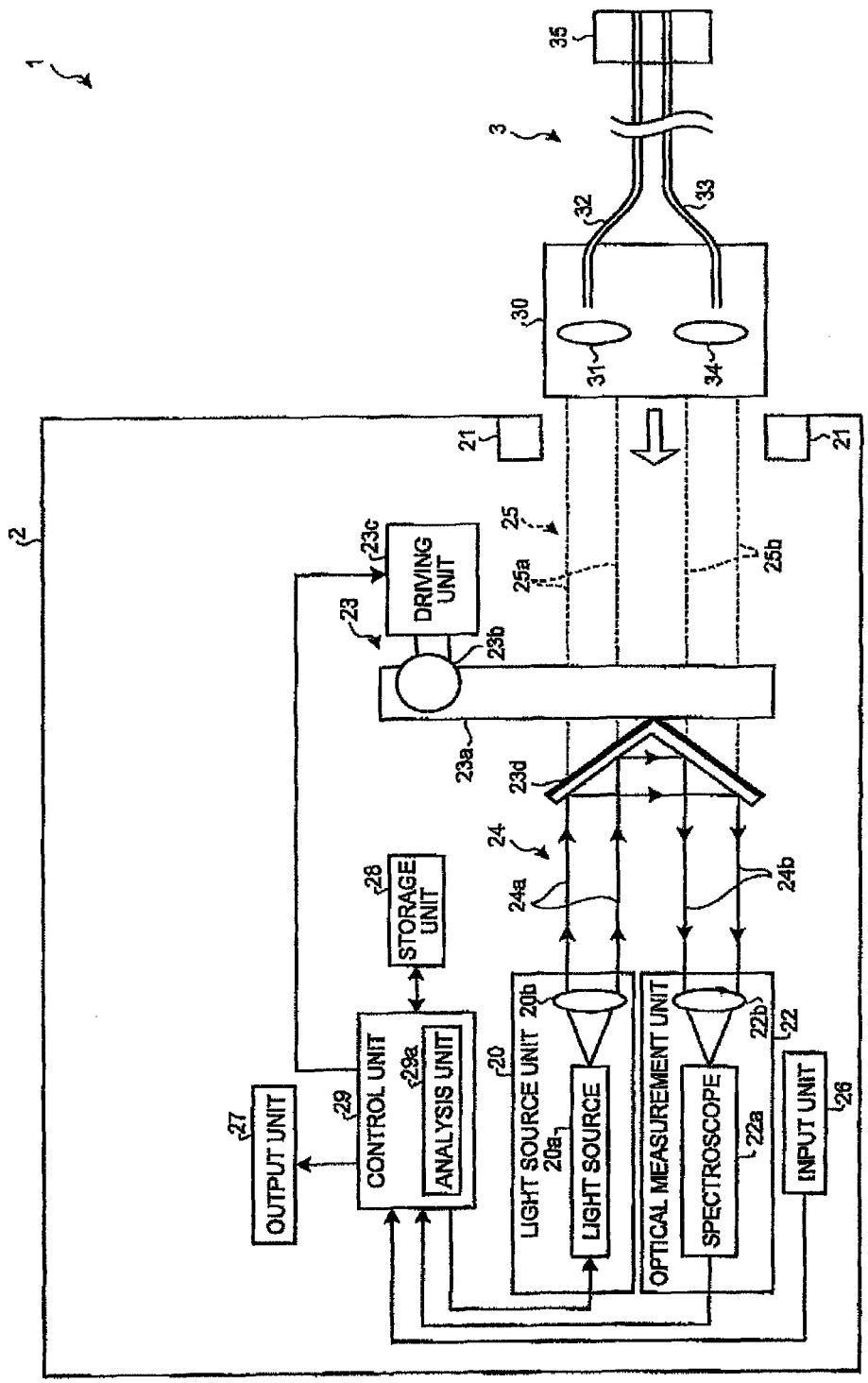
FIG. 1 is a schematic diagram illustrating a schematic configuration of the optical measurement system according to a first embodiment of the invention.

Hereinafter, an optical measurement system and an optical measurement apparatus according to an exemplary embodiment of the invention (hereinafter, referred to as an "embodiment") will be described with reference to the accompanying drawings. The invention is not limited to the embodiments described below. In the description of drawings, like reference numerals denote like elements.

First Embodiment

FIG. 1 is a schematic diagram illustrating a schematic configuration of the optical measurement system according to a first embodiment of the invention. As illustrated in FIG. 1, an optical measurement system 1 includes an optical measurement apparatus 2 that performs optical measurement by irradiating illumination light onto tissue and measuring reflection light and/or scattering light of the illumination light (hereinafter, referred to as "detection light") reflected or scattered by the tissue and a measurement probe 3 introduced into a subject.

The optical measurement apparatus 2 includes a light source unit 20 that emits illumination light onto tissue, a connector 21 for connecting the measurement probe 3, an optical measurement unit 22 that measures detection light incident through the measurement probe 3, an optical path switching unit 23 that switches the optical path of the illumination light emitted by the light source unit 20, a first optical path 24 that transmits the illumination light from the light source unit 20 to the optical measurement unit 22, a second optical path 25 that transmits the illumination light from the light source unit 20 to the measurement probe 3 and transmits the detection light incident through the measurement probe 3 to the optical measurement unit 22, an input unit 26 that receives input of various types of information of the optical measurement apparatus 2, an output unit 27 that outputs the measurement value of tissue or information regarding the optical measurement apparatus 2, a storage unit 28 that stores various types of information, and a control unit 29 that controls the operation of the optical measurement apparatus 2.

The light source unit 20 includes an incoherent light source 20a such as a white LED (light-emitting diode) or a xenon lamp and a collimator lens 20b. The light source unit 20 emits illumination light onto the first or second optical path 24 or 25.

The connector 21 includes an elastic member and the like. The connector 21 is used to detachably connect to the measurement probe 3. The connector 21 may output, to the control unit 29, information regarding whether or not the measurement probe 3 is connected. This information includes, for example, a detection signal obtained by detecting the measurement probe 3.

The optical measurement unit 22 includes a spectroscope 22a and a condensing lens 22b. The optical measurement unit 22 measures the illumination light transmitted from the first optical path 24 or the detection light transmitted from the second optical path 25 to measure spectral components of the illumination light or the detection light and the like. The optical measurement unit 22 outputs the measurement value obtained by measuring the illumination light or the detection light to the control unit 29.

The optical path switching unit 23 switches the optical path of the illumination light emitted by the light source unit 20. The optical path switching unit 23 includes a plate member 23a forwardly and backwardly movable across the second optical path 25, a rotating portion 23b for vertically moving the plate member 23a by rotation, a driving unit 23c for driving the rotating portion 23b, and a reflection member 23d provided in the side surface of the plate member 23a to reflect the illumination light emitted by the light source unit 20 to the optical measurement unit 22. The reflection member 23d includes a mirror having a high reflectance surface for the illumination light or a diffuser that diffuses the illumination light. The reflection member 23d has two surfaces integrated such that corresponding end portions have a predetermined angle, for example, 90°. In addition, one surface of the reflection member 23d may have a mirror, and the other surface may have a diffuser.

The first optical path 24 transmits the illumination light emitted by the light source unit 20 to the optical measurement unit 22. The first optical path 24 includes a first illumination optical path 24a that transmits the illumination light emitted by the light source unit 20 to the reflection member 23d of the optical path switching unit 23, and a first reflectance optical path 24b that transmits the illumination light reflected by the reflection member 23d to the optical measurement unit 22. The first optical path 24 transmits the illumination light emitted by the light source unit 20 without using the measurement probe 3 to the optical measurement unit 22.

The second optical path 25 transmits the illumination light emitted by the light source unit 20 to the measurement probe 3, and transmits the detection light incident through the measurement probe 3 to the optical measurement unit 22. The second optical path 25 includes a second illumination optical path 25a that transmits the illumination light emitted by the light source unit 20 to the measurement probe 3 and a second reflectance optical path 25b that transmits the detection light incident through the measurement probe 3 to the optical measurement unit 22.

The input unit 26 includes a keyboard, a mouse, and the like. The input unit 26 receives various types of information on the optical measurement apparatus 2 from a user.

The output unit 27 includes a display, a lamp, a loudspeaker, and the like. The output unit 27 outputs the measurement value of tissue or various types of information regarding the optical measurement apparatus 2. Specifically, the output unit 27 outputs various types of information regarding the optical measurement apparatus 2 using sound, images, light, and the like.

The storage unit 28 includes a hard disk and semiconductor memory such as RAM (random access memory). The storage unit 28 stores various programs executed by the optical measurement apparatus 2, a measurement value of tissue, calibration processing information, and the like.

The control unit 29 includes a CPU (central processing unit). The control unit 29 transfers instructions or data for each unit of the optical measurement apparatus 2 and the like to collectively control the operation of the optical measurement apparatus 2. The control unit 29 has an analysis unit 29a. The analysis unit 29a analyzes spectral components and the like of the detection light based on the measurement value output from the optical measurement unit 22 to analyze a composition and the like of tissue.

The measurement probe 3 includes a base end portion 30 connected to the connector 21 of the optical measurement apparatus 2, a condensing lens 31 that condenses the illumination light transmitted from the second illumination optical path 25a, an illumination optical fiber 32 that transmits the illumination light condensed by the condensing lens 31 and irradiates the transmitted light onto tissue, a detection optical fiber 33 that transmits the incident detection light reflected by tissue, a collimator lens 34 that collimates the detection light transmitted from the detection optical fiber 33, and a leading end portion 35 where edge faces of the detection optical fiber 33 and the illumination optical fiber 32 are exposed. The measurement probe 3 transmits the illumination light emitted by the light source unit 20 to the leading end portion 35 and transmits the detection light incident through the leading end portion 35 to the optical measurement unit 22.

A manipulation sequence of the optical measurement system 1 having the aforementioned configuration will be described. First, a user drives the optical path switching unit 23 by manipulating the input unit 26 before the measurement probe 3 is connected to the optical measurement apparatus 2. In this case, as illustrated in FIG. 1, the control unit 29 drives the driving unit 23c in response to the instruction signal output from the input unit 26 to forwardly move the plate member 23a up to the optical path of the illumination light irradiated by the light source unit 20 so as to connect the first illumination optical path 24a and the first reflectance optical path 24b. As a result, the illumination light emitted by the light source unit 20 is transmitted to the optical measurement unit 22 through the first optical path 24.

Subsequently, the optical measurement unit 22 measures the illumination light transmitted through the first optical path 24 and outputs the measurement value of the illumination light to the control unit 29. Here, the measurement value refers to a spectral component of the illumination light and the like.

Then, the control unit 29 outputs the measurement value output from the optical measurement unit 22 to the output unit 27. As a result, a user determines whether or not abnormality occurs in the optical measurement apparatus 2 based on the measurement value output by the output unit 27. Specifically, a user determines that the condition of the optical measurement apparatus 2 is abnormal if the measurement value output by the output unit 27 is low. Abnormality of the optical measurement apparatus 2 includes a breakdown of the light source of the light source unit 20, a failure of the spectroscope 22a, and the like.

Figure 2:
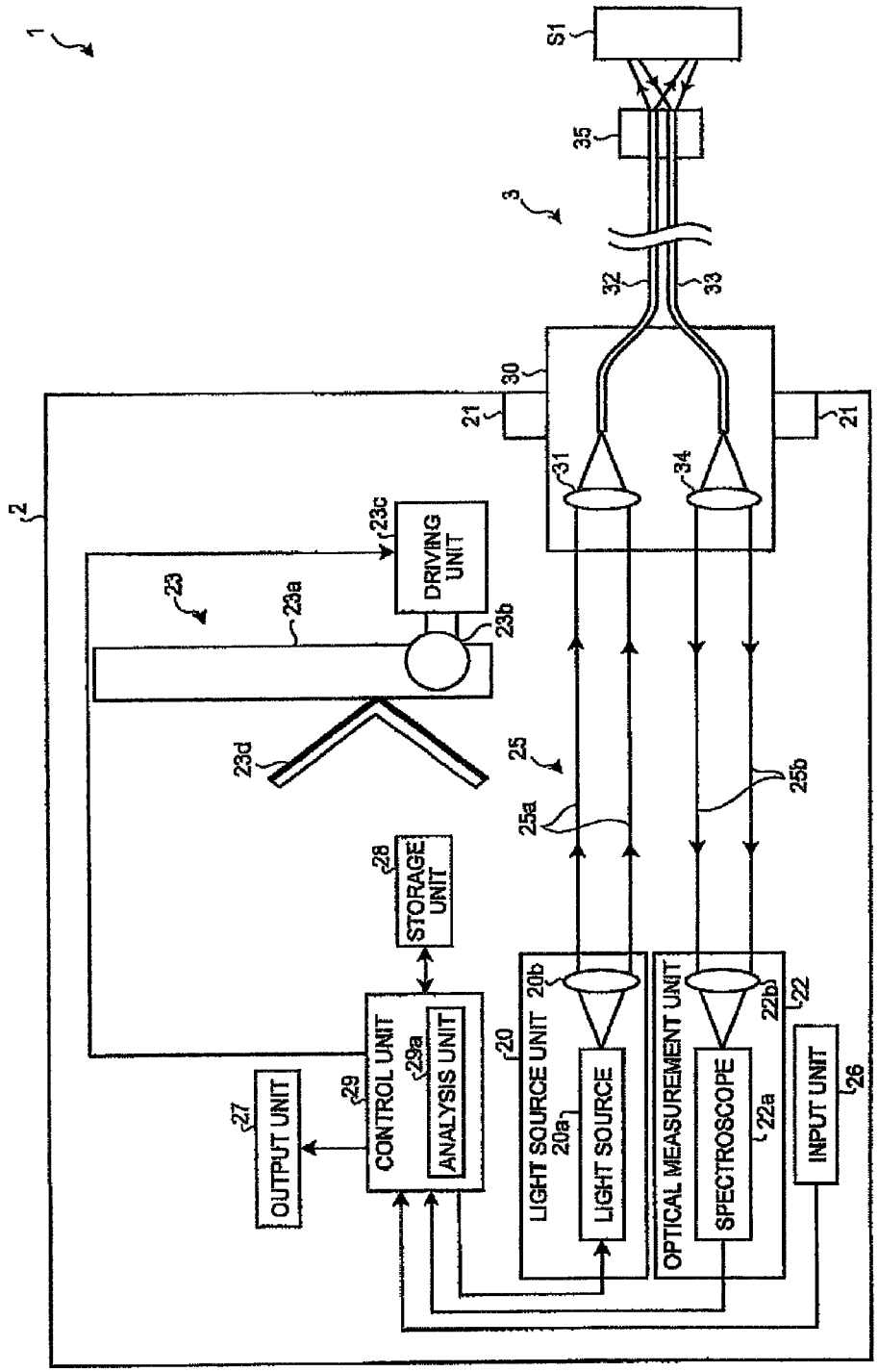
FIG. 2 is a diagram illustrating a condition that a measurement probe is connected to the optical measurement apparatus according to the first embodiment of the invention.

After the condition of the optical measurement apparatus 2 is determined, a user connects the base end portion 30 of the measurement probe 3 to the connector 21 of the optical measurement apparatus 2. Specifically, as illustrated in FIG. 2, a user connects the base end portion 30 of the measurement probe 3 to the connector 21 of the optical measurement apparatus 2.

Subsequently, the control unit 29 drives the driving unit 23c in response to the instruction signal output from the input unit 26 to backwardly move the plate member 23a from the first optical path 24. As a result, the optical path of the illumination light emitted by the light source unit 20 is transmitted to the second optical path 25.

Then, the light source unit 20 emits the illumination light onto the calibration member S1 through the second optical path 25 and the measurement probe 3, and the optical measurement unit 22 outputs the measurement value obtained by measuring the detection light of the calibration member S1 incident through the measurement probe 3 to the control unit 29. Here, the calibration member is a member of which a white board or a surface has reflectance already known for the illumination light.

Subsequently, the control unit 29 outputs the measurement value of the calibration member S1 from the optical measurement unit 22 to the output unit 27. As a result, a user determines abnormality of the measurement probe 3 such as a breakdown of the illumination optical fiber 32 of the measurement probe 3 based on the measurement value of the calibration member S1 output by the output unit 27.

After it is determined that the condition of the measurement probe 3 connected to the optical measurement apparatus 2 is normal, a user starts measurement for the measurement target using the optical measurement system 1. Specifically, a user introduces the measurement probe 3 into a subject through a treatment tool insertion portion (channel) of an endoscope device and starts measurement. In response to start of the measurement, the control unit 29 outputs the measurement value of tissue to the output unit 27. As a result, a user diagnoses whether or not there is diseased tissue.

As described above, according to the first embodiment, the optical path switching unit 23 switches the optical path of the illumination light emitted by the light source unit 20 to the first or second optical path 24 or 25, so that it is possible to recognize abnormality in the optical measurement apparatus 2. As a result, even when abnormality occurs in the optical measurement apparatus 2 or the measurement probe 3, it is possible to specify an abnormal portion.

In addition, according to the first embodiment, it is possible to recognize abnormality in the optical measurement apparatus 2, for example, before a disposable measurement probe 3 is connected to the optical measurement apparatus 2. Therefore, it is possible to prevent, in advance, cumbersomeness generated by opening the measurement probe 3 enveloped by a casing and the like and connecting it or wastefulness of the measurement probe 3.

In addition, according to the first embodiment, the control unit 29 drives the optical path switching unit 23 in response to the instruction signal output from the input unit 26 to switch the optical path of the illumination light emitted by the light source unit 20 into the first or second optical path 24 or 25. However, the optical path switching unit 23 may be driven by providing a vertical movement dial and the like for vertically moving the plate member 23a and manually manipulating the vertical movement dial by a user to switch the optical path used for the light emitted by the light source unit 20 into the first or second optical path 24 or 25.

Figure 3:
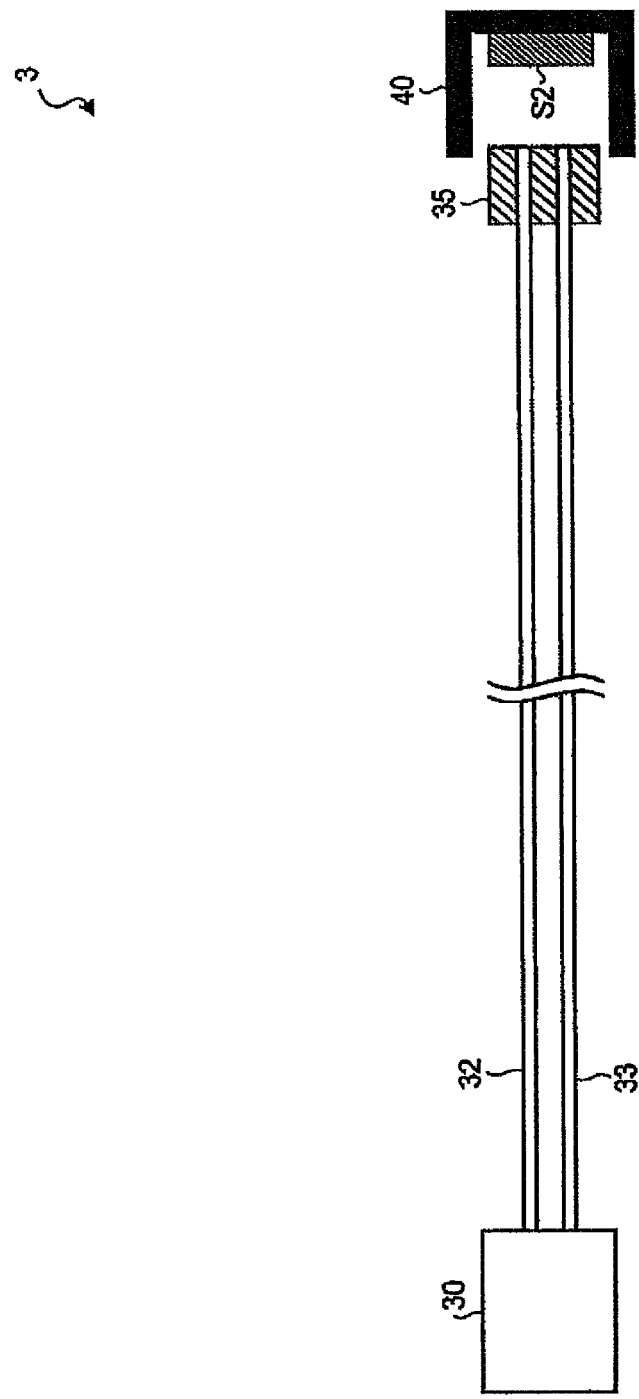
FIG. 3 is a diagram illustrating a schematic configuration of the measurement probe according to a modification of the first embodiment of the invention.

Although abnormality of the measurement probe 3 is determined by directly irradiating the illumination light onto the calibration member S1 according to the first embodiment, abnormality of the measurement probe 3 may be determined by providing a calibration member S2 in a cap portion 40 (calibration module) detachably provided in the leading end portion 35 of the measurement probe 3 and installing the cap portion 40 in the leading end portion 35 before starting the measurement of tissue as illustrated in FIG. 3. In addition, a connector or the like for providing a constant distance between the calibration member 82 and the leading end portion 35 of the measurement probe 3 may be provided in the cap portion 40. In this case, it is possible to more reliably determine whether or not abnormality occurs in the second optical path 25.

Although a user determines abnormality of the optical measurement apparatus 2 or the measurement probe 3 by outputting the measurement value from the output unit 27 according to the first embodiment, the output unit 27 may output information indicating abnormality in the optical measurement apparatus 2 or the measurement probe 3, for example, when the measurement value measured by the optical measurement unit 22 is smaller than a predetermined threshold value.

Second Embodiment

Figure 4:
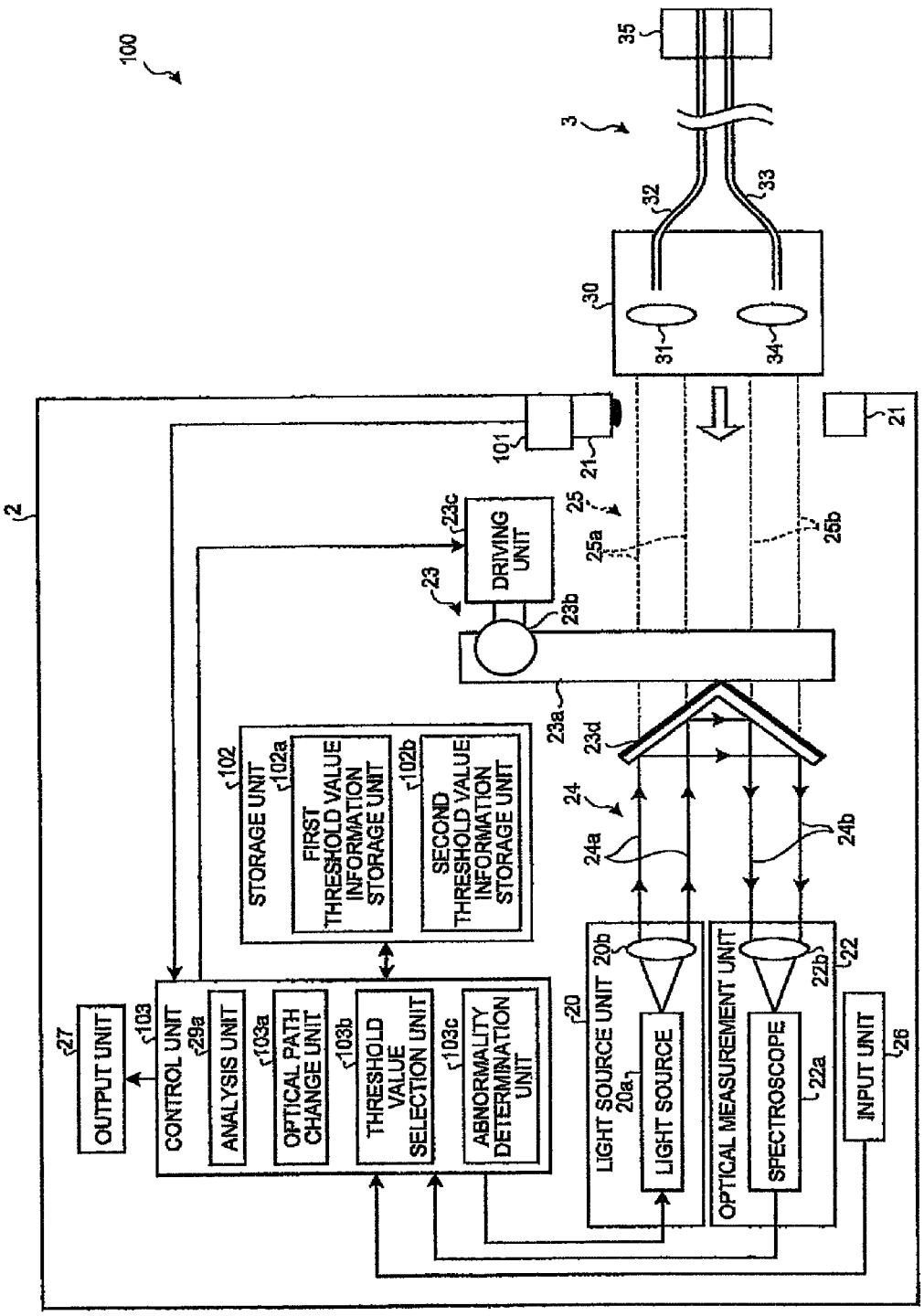
FIG. 4 is a schematic diagram illustrating a schematic configuration of the optical measurement system according to a second embodiment of the invention.

Next, a second embodiment of the invention will be described. FIG. 4 is a schematic diagram illustrating a schematic configuration of an optical measurement system 100 according to the second embodiment. In FIG. 4, like reference numerals denote like elements as in the configuration of the optical measurement system 1 described above in the first embodiment, and description thereof will not be repeated.

As illustrated in FIG. 4, the optical measurement system 100 includes a probe detection unit 101, a storage unit 102, and a control unit 103.

The probe detection unit 101 is provided in the connector 21 and outputs, to the control unit 103, information regarding whether or not the measurement probe 3 is connected. This information is a detection signal obtained by detecting the base end portion 30 of the measurement probe 3.

Figure 5:
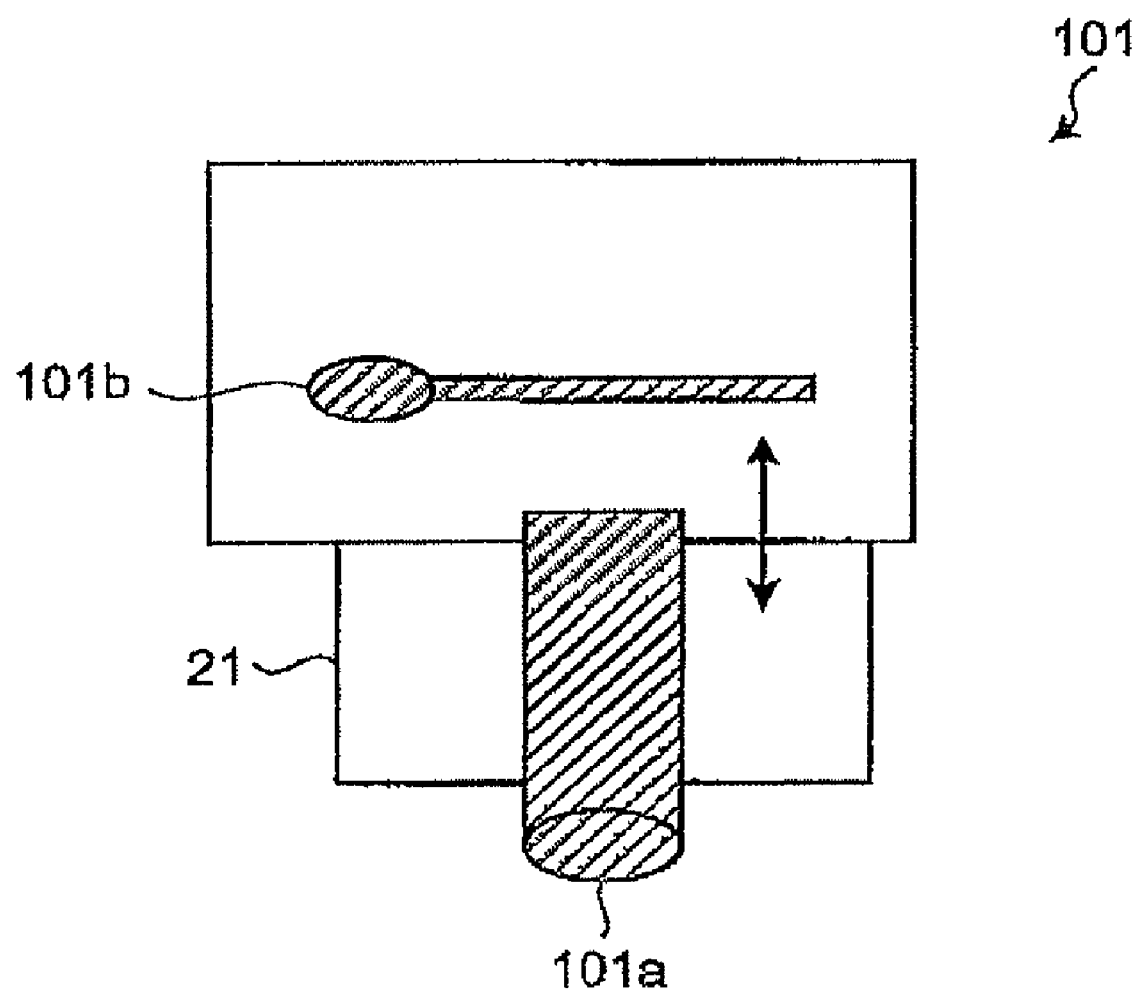
FIG. 5 is a schematic diagram illustrating a schematic configuration of the probe detection unit of FIG. 4.

FIG. 5 is a schematic diagram illustrating a schematic configuration of the probe detection unit 101. As illustrated in FIG. 5, the probe detection unit 101 is provided to forwardly and backwardly move in a direction perpendicular to an insertion direction in which the base end portion 30 of the measurement probe 3 is inserted, and includes a protrusion 101a making contact with the base end portion 30 of the measurement probe 3 and a contact sensor 101b that outputs, to the control unit 103, a detection signal obtained by detecting connection of the measurement probe 3 when the protrusion 101a makes contact with the base end portion 30 of the measurement probe 3.

The storage unit 102 includes a first threshold value information storage unit 102a that stores the first threshold value information indicating the measurement value of the illumination light measured by the optical measurement unit 22 when the first optical path 24 is normal and a second threshold value information storage unit 102b that stores the second threshold value information indicating the measurement value of the detection light measured by the optical measurement unit 22 when the second optical path 25 is normal.

The control unit 103 includes an optical path change unit 103a, a threshold value selection unit 103b, and an abnormality determination unit 103c.

The optical path change unit 103a drives the optical path switching unit 23 depending on the detection result of the probe detection unit 101 to switch the optical path of the illumination light emitted by the light source unit 20 into the first or second optical path 24 or 25. Specifically, the optical path change unit 103a switches the optical path of the illumination light emitted by the light source unit 20 into the second optical path 25 when the probe detection unit 101 detects connection of the base end portion 30 of the measurement probe 3. On the contrary, the optical path change unit 103a switches the optical path of the illumination light emitted by the light source unit 20 into the first optical path 24 when the probe detection unit 101 does not detect connection of the base end portion 30 of the measurement probe 3.

The threshold value selection unit 103b selectively obtains the first threshold value information or the second threshold value information stored in the storage unit 102 depending on the optical path of the illumination light changed by the optical path change unit 103a.

The abnormality determination unit 103c determines whether or not abnormality occurs in the first or second optical path 24 or 25. Specifically, the abnormality determination unit 103c determines that abnormality occurs in the first optical path 24 if the measurement value measured by the optical measurement unit 22 is not equal to or greater than the first threshold value when the optical path change unit 103a changes the optical path of the illumination light into the first optical path 24. The abnormality determination unit 103c determines that abnormality occurs in the second optical path 25 if the measurement value measured by the optical measurement unit 22 is not equal to or greater than the second threshold value when the optical path change unit 103a changes the optical path of the illumination light into the second optical path 25.

Figure 6:
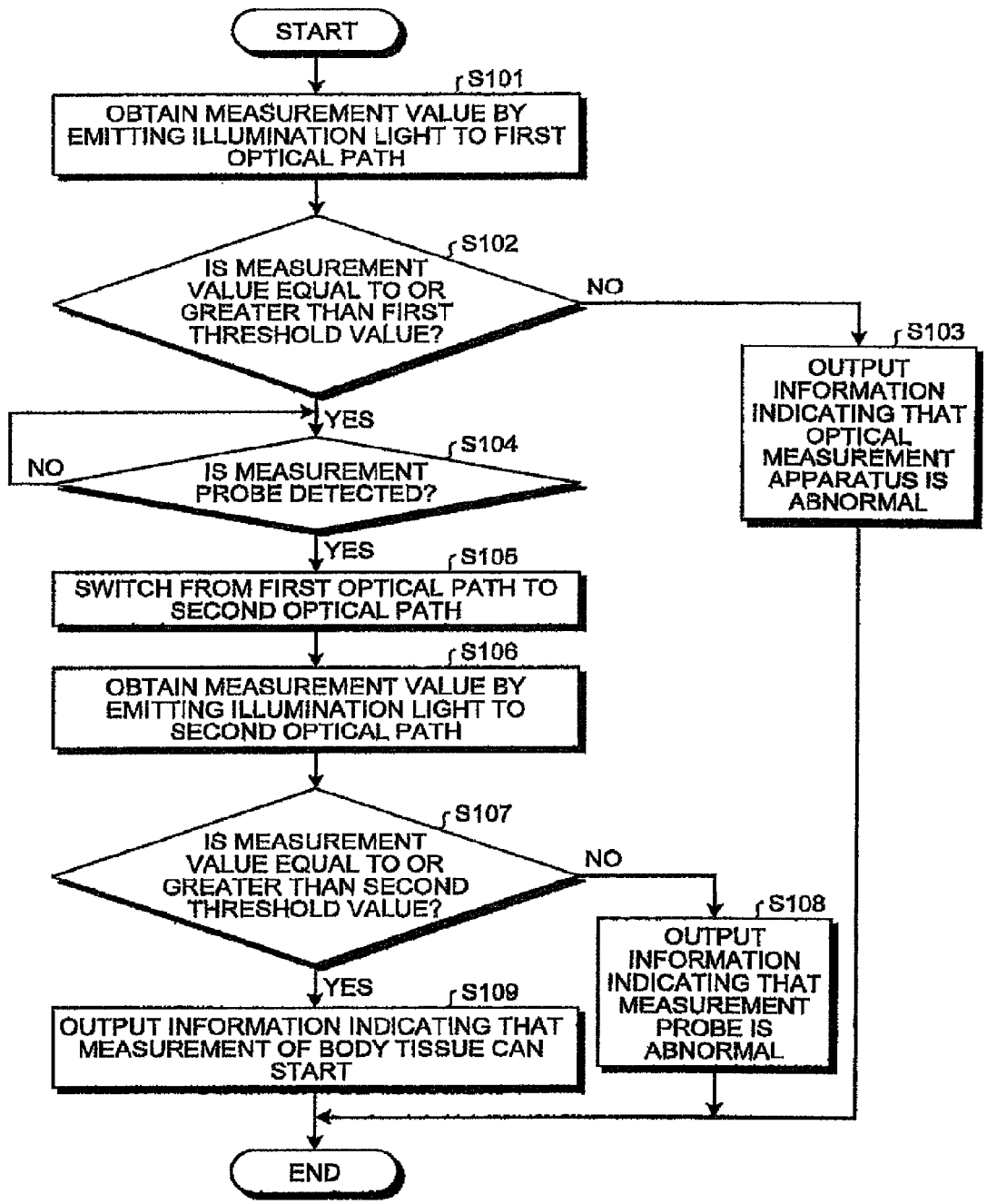
FIG. 6 is a flowchart illustrating an outline of the process performed by the optical measurement system according to the second embodiment.

An outline of the process performed by the optical measurement system 100 having the aforementioned configuration will be described. FIG. 6 is a flowchart illustrating an outline of the process performed by the optical measurement system 100.

As illustrated in FIG. 6, first, the control unit 103 emits the illumination light of the light source unit 20 to the first optical path 24 to obtain the measurement value of the optical measurement unit 22 (step S101).

Subsequently, the abnormality determination unit 103c determines whether or not the measurement value of the optical measurement unit 22 is equal to or greater than the first threshold value (step S102). It the measurement value of the optical measurement unit 22 is not equal to or greater than the first threshold value (NO in step S102), the control unit 103 outputs, to the output unit 27, information indicating that abnormality occurs in the optical measurement apparatus 2 (step S103), and the optical measurement system 100 terminates this process. As a result, a user can recognize that abnormality occurs in the optical measurement apparatus 2 before the measurement probe 3 is connected to the optical measurement apparatus 2.

Otherwise, if the measurement value of the optical measurement unit 22 is equal to or greater than the first threshold value (YES in step S102), the control unit 103 determines whether or not the probe detection unit 101 detects connection of the measurement probe 3 (step S104). If the probe detection unit 101 does not detect connection of the measurement probe 3 (NO in step S104), the control unit 103 repeats this determination. Otherwise, if the probe detection unit 101 detects connection of the measurement probe 3 (YES in step S104), the optical measurement system 100 advances the process to step S105.

Figure 7:
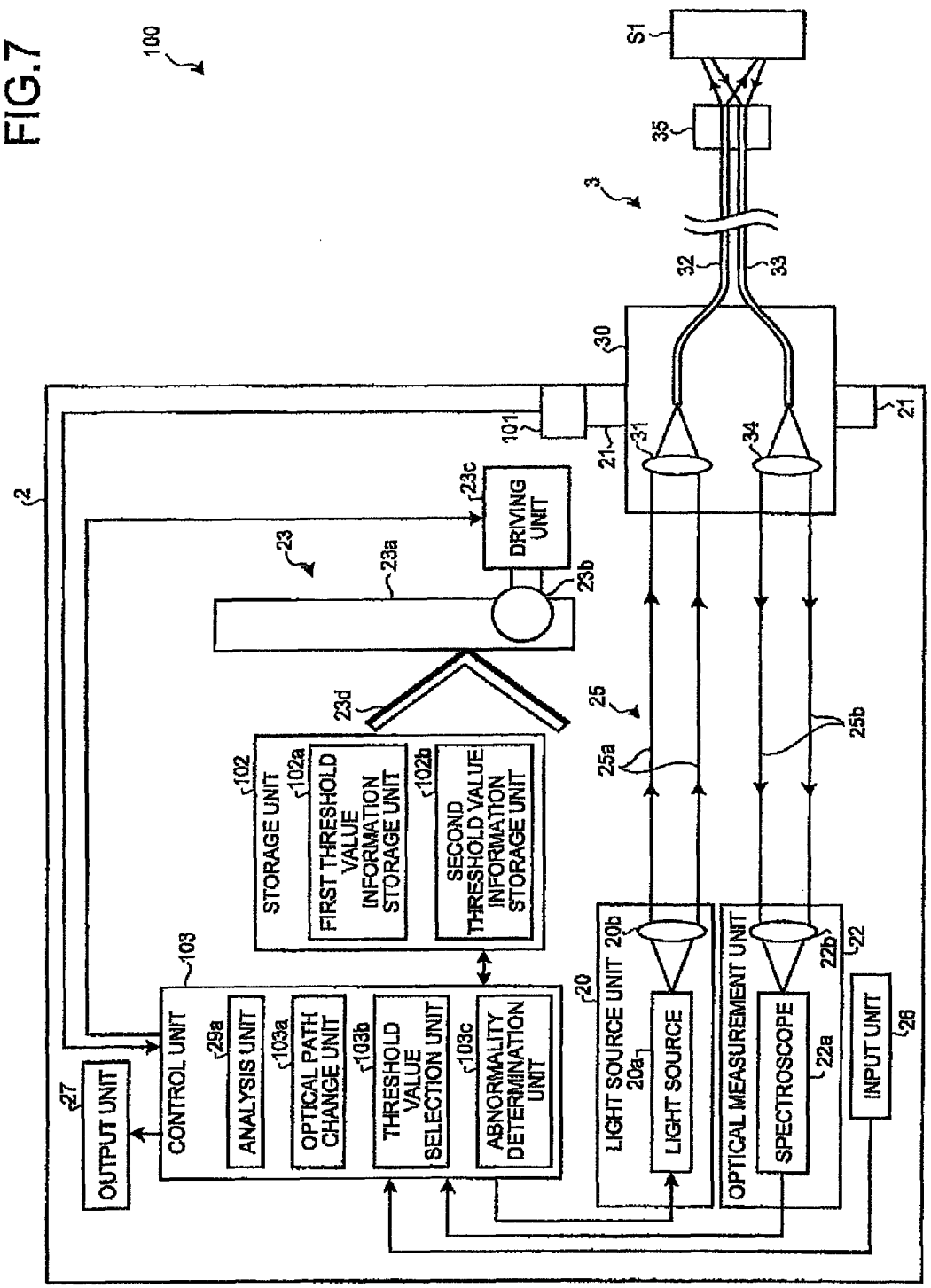
FIG. 7 is a diagram illustrating a condition that the measurement probe is connected to the optical measurement apparatus according to the second embodiment of the invention.

Subsequently, the optical path change unit 103a switches the optical path of the illumination light emitted by the light source unit 20 from the first optical path 24 into the second optical path 25 by driving the optical path switching unit 23 (step S105), and the control unit 103 obtains the measurement value of the optical measurement unit 22 by emitting the illumination light of the light source unit 20 to the first optical path 24 (step S106). Specifically, as illustrated in FIG. 7, the optical path switching unit 23 switches the optical path of the illumination light from the first optical path 24 into the second optical path 25 by backwardly moving the plate member 23a from the optical path of the illumination light emitted by the light source unit 20.

Then, the abnormality determination unit 103c determines whether or not the measurement value of the optical measurement unit 22 is equal to or greater than the second threshold value (step S107). If the measurement value of the optical measurement unit 22 is not equal to or greater than the second threshold value (NO in step S107), the control unit 103 outputs, to the output unit 27, information indicating that abnormality occurs in the measurement probe 3 (step S108), and the optical measurement system 100 terminates this process. As a result, a user can recognize that abnormality occurs in the measurement probe 3 connected to the optical measurement apparatus 2.

Otherwise, if the measurement value of the optical measurement unit 22 is equal to or greater than the second threshold value (YES in step S107), the control unit 103 outputs, to the output unit 27, information indicating that the measurement of tissue using the optical measurement system 100 can start (step S109), and the optical measurement system 100 terminates this process. As a result, a user starts the measurement of tissue using the optical measurement system 100.

According to the second embodiment described above, the abnormality determination unit 103c determines whether or not abnormality occurs in the first or second optical path 24 or 25 by referencing the optical path for transmitting the illumination light changed by the optical path change unit 103a and the first or second threshold value information stored in the storage unit 102. Therefore, similar to the first embodiment described above, it is possible to recognize abnormality in the optical measurement apparatus 2. As a result, it is possible to easily specify an abnormal portion even when abnormality occurs in the optical measurement apparatus 2 or the measurement probe 3.

In addition, according to the second embodiment, the optical path change unit 103a switches the optical path of the illumination light emitted by the light source unit 20 into the first or second optical path 24 or 25 by driving the optical path switching unit 23 depending on the detection result of the probe detection unit 101. For this reason, the optical path change unit 103a automatically changes the optical path of the illumination light into the first optical path 24 as power is supplied to the optical measurement apparatus 2. As a result, a user can recognize abnormality in the optical measurement apparatus 2 as power is supplied to the optical measurement apparatus 2. Therefore, it is possible to in advance prevent cumbersomeness generated by opening the measurement probe 3 enveloped by a casing and the like and connecting it or wastefulness of the measurement probe 3 when the measurement of tissue is performed using the disposable measurement probe 3.

In addition, although the probe detection unit 101 includes a contact sensor according to the second embodiment, for example, the probe detection unit 101 may include a switch such as an electrode or an infrared sensor.

Third Embodiment

Figure 8:
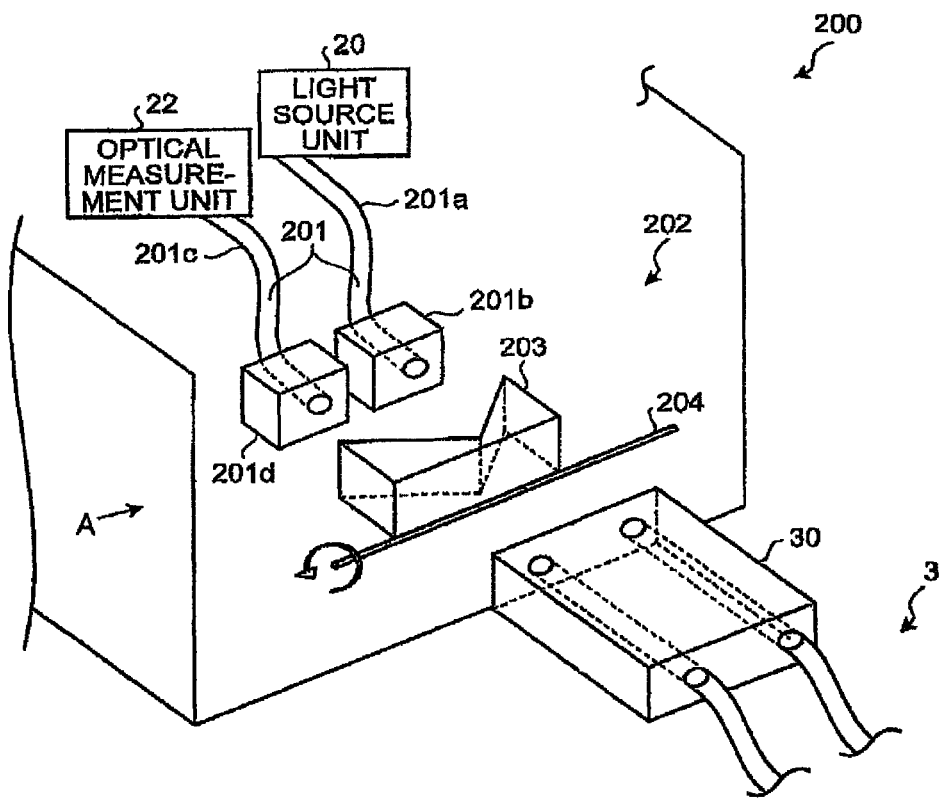
FIG. 8 is a partially cut-away perspective view schematically illustrating the optical measurement system according to a third embodiment of the invention.
Figure 9:
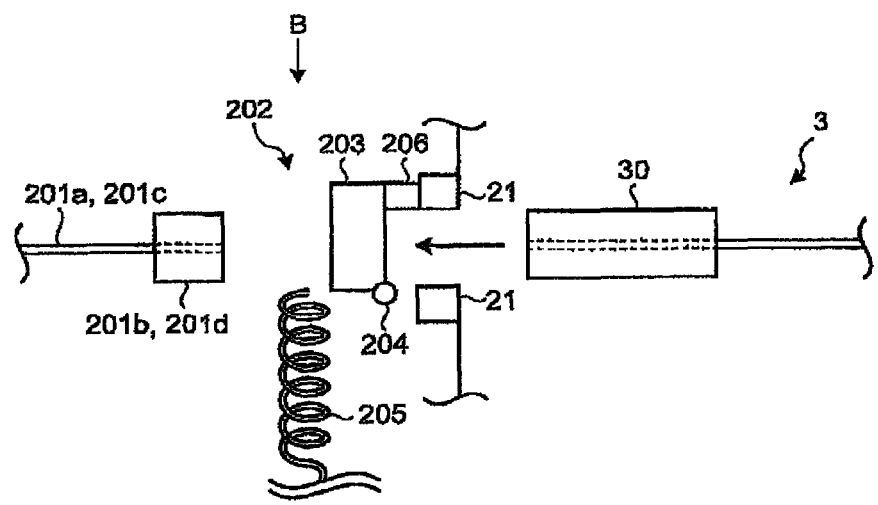
FIG. 9 is a cross-sectional view schematically illustrating a cross section as seen from an arrow A of FIG. 8.

Next, a third embodiment of the invention will be described. FIG. 8 is a partially cut-away perspective view schematically illustrating an optical measurement system 200 according to the third embodiment. FIG. 9 is a cross-sectional view schematically illustrating a cross section as seen from an arrow A of FIG. 8. In FIGS. 8 and 9, like reference numerals denote like elements as in the configuration of the optical measurement system described in the aforementioned embodiments, and description thereof will not be repeated.

As illustrated in FIGS. 8 and 9, the optical measurement system 200 includes a first optical path 201 and an optical path switching unit 202.

The first optical path 201 transmits the illumination light emitted by the light source unit 20 to the optical measurement unit 22. The first optical path 201 includes an illumination optical fiber 201a that transmits illumination light, an illumination optical fiber support portion 201b that supports the illumination optical fiber 201a, a detection optical fiber 201c that transmits illumination light or detection light, and a detection optical fiber support portion 201d that supports the detection optical fiber 201c.

The optical path switching unit 202 is arranged in the middle of the optical path between the connector 21 and the light source unit 20 or the optical measurement unit 22. The optical path switching unit 202 includes a reflection member 203 arranged movably between an insertion position for insertion into the optical path between the connector 21 and the light source unit 20 or the optical measurement unit 22 or a retreating position for retreating from the optical path between the connector 21 and the light source unit 20 or the optical measurement unit 22, a support member 204 that rotatably supports the reflection member 203, an elastic member 205 that biases the reflection member 203 toward the optical path, and a stopper 206 that prevents the reflection member 203 from getting out to the connector 21 side by the elastic member 205.

Figure 10:
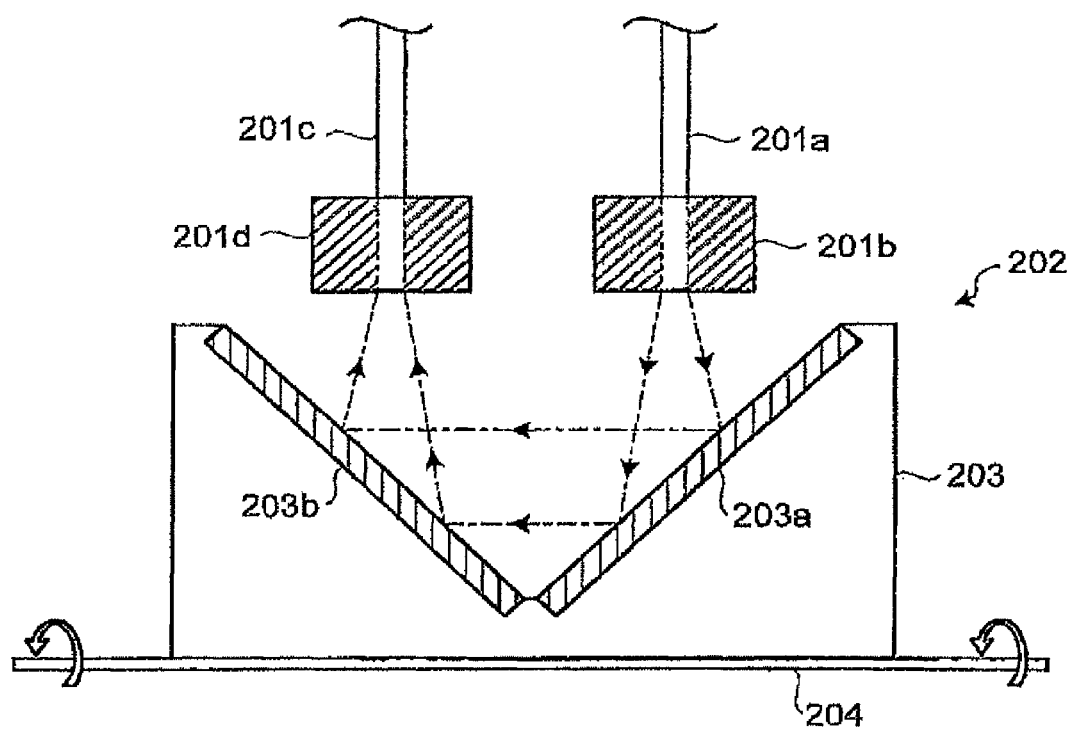
FIG. 10 is a schematic diagram as seen from an arrow B of FIG. 9.

FIG. 10 is a schematic diagram as seen from the arrow B of FIG. 9. As illustrated in FIG. 10, the reflection member 203 includes first and second reflection members 203a and 203b. The first and second reflection members 203a and 203b are formed such that end portions thereof make a predetermined angle, for example, 90°. The first and second reflection members 203a and 203b include a mirror or a diffuser. The first reflection member 203a reflects, to the second reflection member 203b, the illumination light emitted by the illumination optical fiber 201a. The second reflection member 203b reflects, to the detection optical fiber 201c, at least a part of the illumination light reflected from the first reflection member 203a.

Figure 11A:
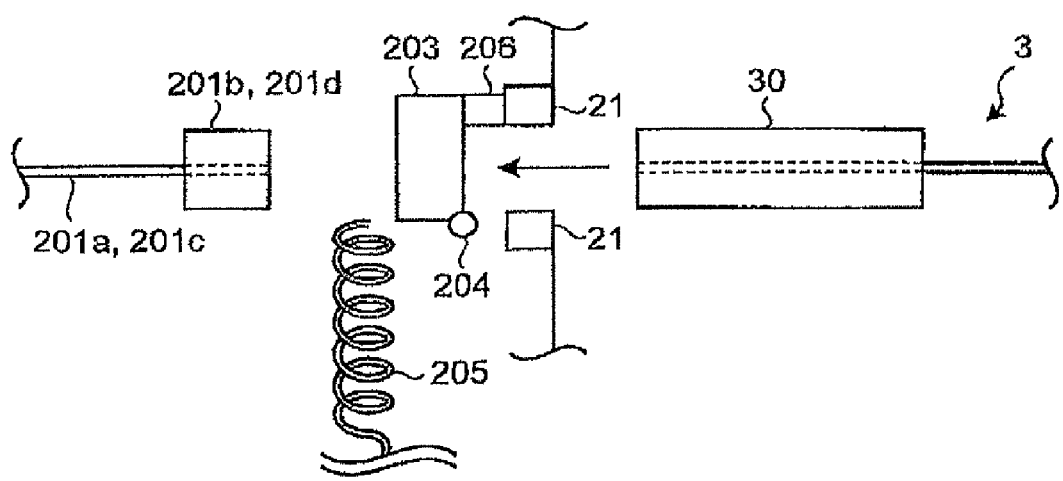
FIGS. 11A and 11B are explanatory diagrams illustrating the operation of the optical path switching unit of FIG. 8.
Figure 11B:
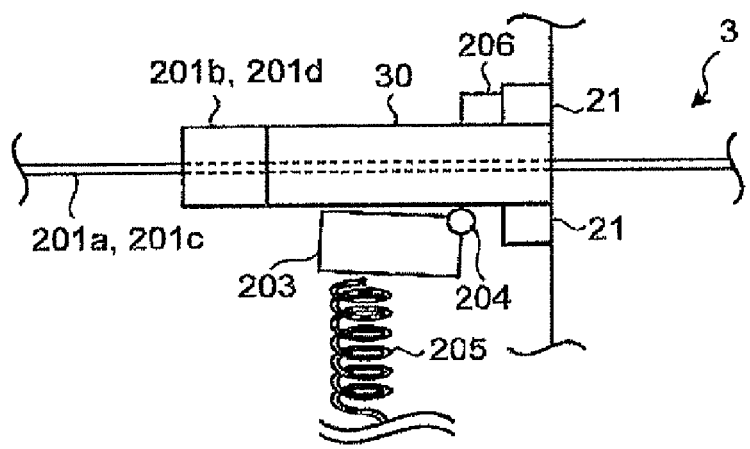

A manipulation sequence of the optical measurement system 200 having the aforementioned configuration will be described. FIGS. 11A and 11B are explanatory diagrams illustrating the operation of the optical path switching unit 202.

First, before the measurement probe 3 is installed in the optical measurement apparatus 2 (refer to FIG. 11A), the control unit 29 causes the light source unit 20 to emit the illumination light. As a result, the illumination light emitted by the light source unit 20 is emitted to the first reflection member 203a through the illumination optical fiber 201a, is incident to the detection optical fiber 201c through the first and second reflection members 203a and 203b, and is transmitted to the optical measurement unit 22.

Subsequently, the optical measurement unit 22 outputs, to the control unit 29, the measurement value of the illumination light obtained by measuring the illumination light transmitted through the first optical path 201, and the control unit 29 outputs, to the output unit 27, the measurement value output from the optical measurement unit 22. As a result, a user determines whether or not abnormality occurs in the optical measurement apparatus 2 based on the measurement value output by the output unit 27. Specifically, a user determines that the condition of the optical measurement apparatus 2 is abnormal if the measurement value output by the output unit 27 is low. The abnormality of the optical measurement apparatus 2 includes a breakdown of the light source of the light source unit 20, a failure of the spectroscope 22a, and the like.

Figure 12:
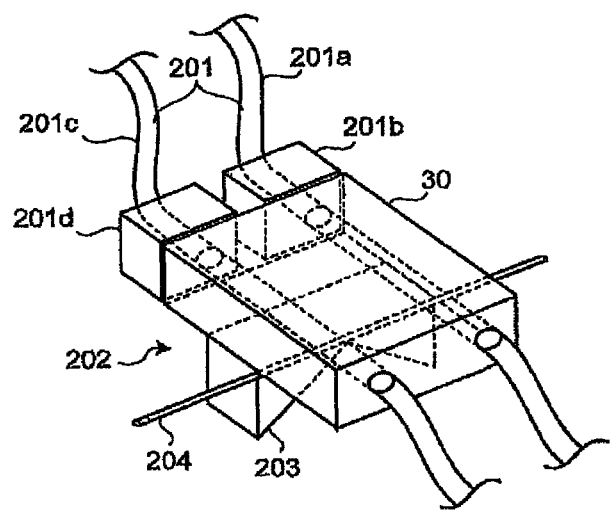
FIG. 12 is a perspective view illustrating a condition that the measurement probe is connected to the optical measurement apparatus according to the third embodiment of the invention.

After the condition of the optical measurement apparatus 2 is determined, a user connects the base end portion 30 of the measurement probe 3 to the connector 21 of the optical measurement apparatus 2 (FIG. 11A→FIG. 11B). In this case, the reflection member 203 is inserted into the base end portion 30 of the measurement probe 3 to move from the insertion position to the retreating position while the elastic member 205 is biased. As a result, since the illumination optical fiber support portion 201b and the detection optical fiber support portion 201d are connected to the base end portion 30 of the measurement probe 3 (refer to FIG. 12), the optical path of the illumination light emitted by the light source unit 20 is transferred to the second optical path 25 (refer to FIG. 2).

Subsequently, the light source unit 20 emits the illumination light to the calibration member S1 through the second optical path 25 and the measurement probe 3 (refer to FIG. 1), and the optical measurement unit 22 outputs, to the control unit 29, the measurement value obtained by measuring the detection light of the calibration member S1 incident through the measurement probe 3.

Then, the control unit 29 outputs, to the output unit 27, the measurement value of the calibration member S1 output from the optical measurement unit 22. As a result, a user determines abnormality of the measurement probe 3 based on the measurement value of the calibration member S1 output by the output unit 27.

After it is determined that the condition of the measurement probe 3 connected to the optical measurement apparatus 2 is normal, a user starts measurement of the measurement target using the optical measurement system 1.

In the third embodiment described above, the optical path switching unit 202 switches the optical path of the illumination light emitted by the light source unit 20 from the first optical path 201 into the second optical path 25 by inserting the base end portion 30 of the measurement probe 3 into the optical path of the light source unit 20 side with pressure and the optical measurement unit 22 side. Therefore, similar to the first embodiment described above, it is possible to recognize abnormality in the optical measurement apparatus 2.

In addition, according to the third embodiment, since the optical path of the illumination light is not perfectly switched into the second optical path 25 if the base end portion 30 of the measurement probe 3 is not connected to the connector 21 of the optical measurement apparatus 2. Therefore, it is possible to determine whether or not abnormality occurs in the optical measurement apparatus 2 as power is supplied to the optical measurement apparatus 2.

Although the first and second reflection members 203a and 203b include a mirror according to the third embodiment, for example, the first reflection member 203a may include a mirror, and the second reflection member 203b may include a diffuser.

Modification of Third Embodiment

Figure 13:
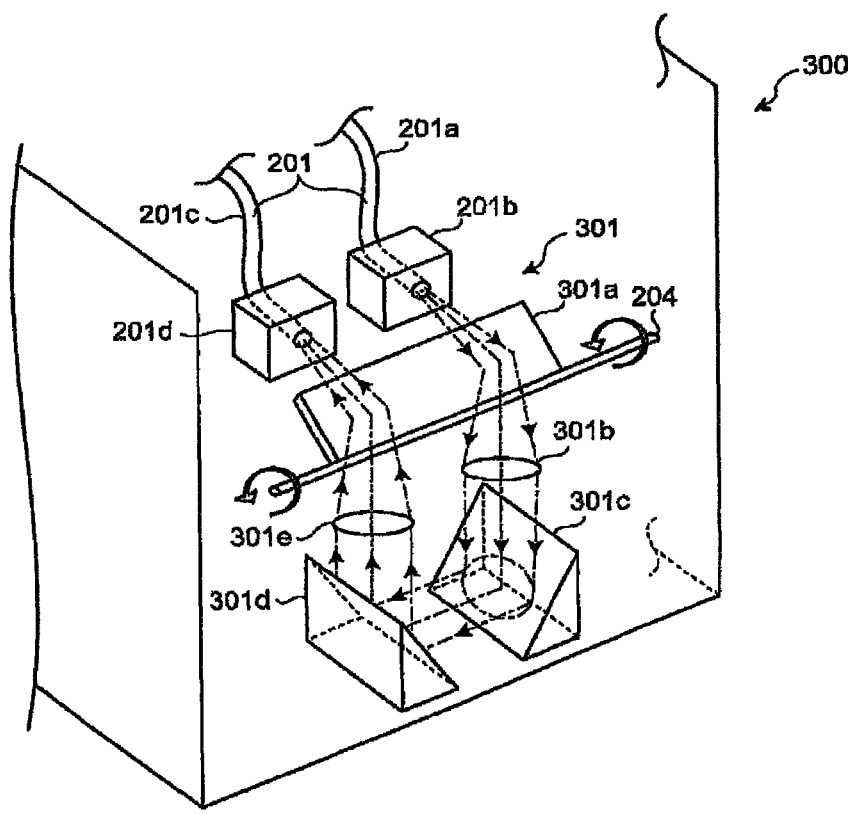
FIG. 13 is a partially cut-away perspective view schematically illustrating the optical measurement system according to a modification of the third embodiment of the invention.
Figure 14:
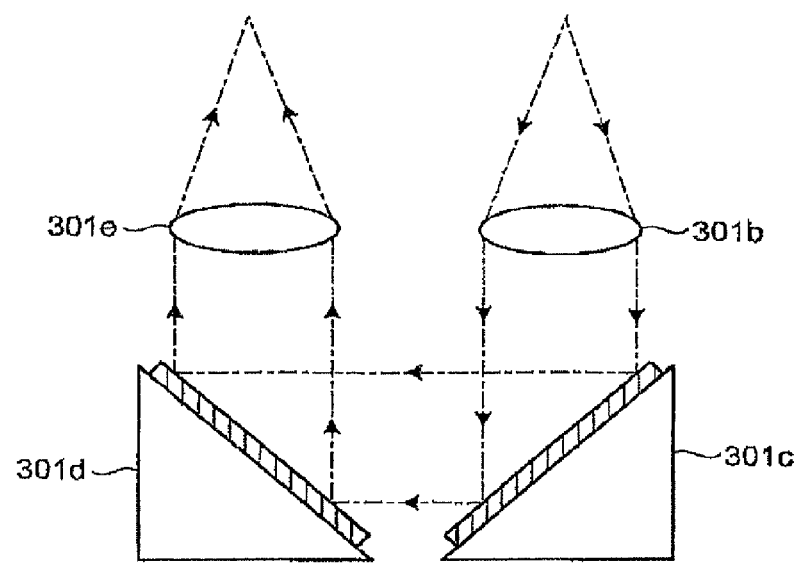
FIG. 14 is a partially enlarged schematic diagram illustrating the optical path switching unit of FIG. 13.

Next, a modification of the third embodiment will be described. FIG. 13 is a partially cut-away perspective view schematically illustrating a part of an optical measurement system 300 according to a modification of the third embodiment. FIG. 14 is a partially enlarged schematic diagram illustrating the optical path switching unit of FIG. 13. In the FIGS. 13 and 14, like reference numerals denote like elements as in the configuration of the optical measurement system described in the aforementioned embodiments, and description thereof will not be repeated.

As illustrated in FIGS. 13 and 14, the optical measurement system 300 includes an optical path switching unit 301. The optical path switching unit 301 is arranged in the middle of the optical path between the connector 21 and the light source unit 20 or the optical measurement unit 22. The optical path switching unit 301 is movably arranged between the insertion position and the retreating position, and includes a reflection member 301a that reflects the illumination light emitted by the light source unit 20, a collimator lens 301b that collimates the illumination light reflected by the reflection member 301a, a first reflection member 301c that reflects the illumination light incident through the collimator lens 301b, a second reflection member 301d that reflects the illumination light reflected by the first reflection member 301c, and a condensing lens 301e that condenses the illumination light reflected by the second reflection member 301d.

A manipulation sequence of the optical measurement system 300 having the aforementioned configuration will be described. According to the modification of the invention, only the optical path of the illumination light emitted by the light source unit 20 is different, and the manipulation sequence is similar to that of the optical measurement system according to the third embodiment described above. For this reason, only the optical path of the illumination light emitted by the light source unit 20 will be described.

First, the illumination light emitted by the light source unit 20 passes through the illumination optical fiber 201a and is reflected at the reflection member 301a.

Subsequently, the illumination light reflected at the reflection member 301a passes through the collimator lens 301b, the first reflection member 301c, the second reflection member 301d, and the condensing lens 301e, and is reflected at the reflection member 301a.

Then, the illumination light reflected at the reflection member 301a is incident to the detection optical fiber 201c and is transmitted to the optical measurement unit 22. As a result, the illumination light emitted by the light source unit 20 is transmitted to the optical measurement unit 22 through the reflection member 301a, the collimator lens 301b, the first reflection member 301c, the second reflection member 301d, the condensing lens 301e, and the reflection member 301a.

In the modification of the third embodiment described above, the optical path switching unit 301 switches the optical path of the illumination light emitted by the light source unit 20 from the first optical path 201 to the second optical path 25 by inserting the base end portion 30 of the measurement probe 3 into the optical path of the light source unit 20 side with pressure and the optical measurement unit 22 side. Therefore, similar to the first embodiment, it is possible to recognize abnormality in the optical measurement apparatus 2 before the measurement probe 3 is connected.

Fourth Embodiment

Figure 15:
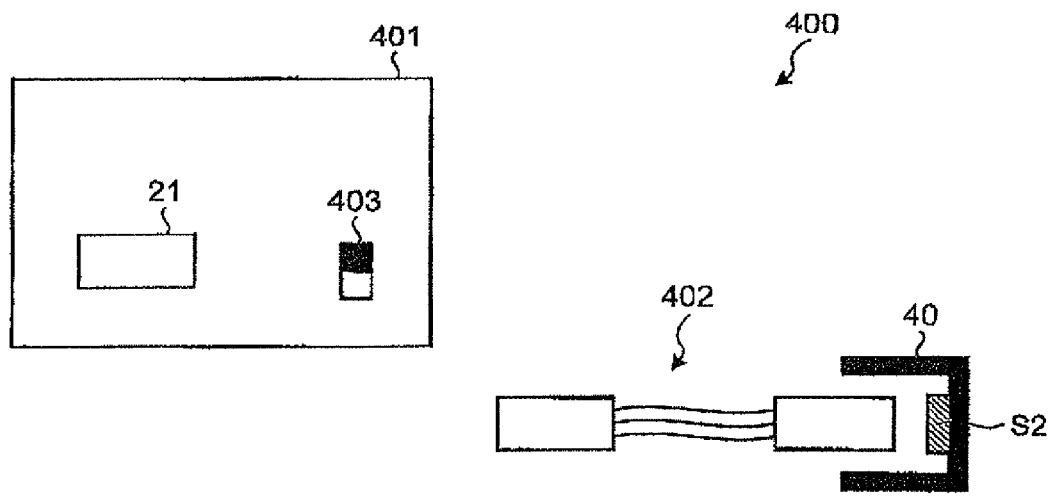
FIG. 15 is a schematic diagram illustrating a schematic configuration of the optical measurement system according to a fourth embodiment of the invention.
Figure 16:
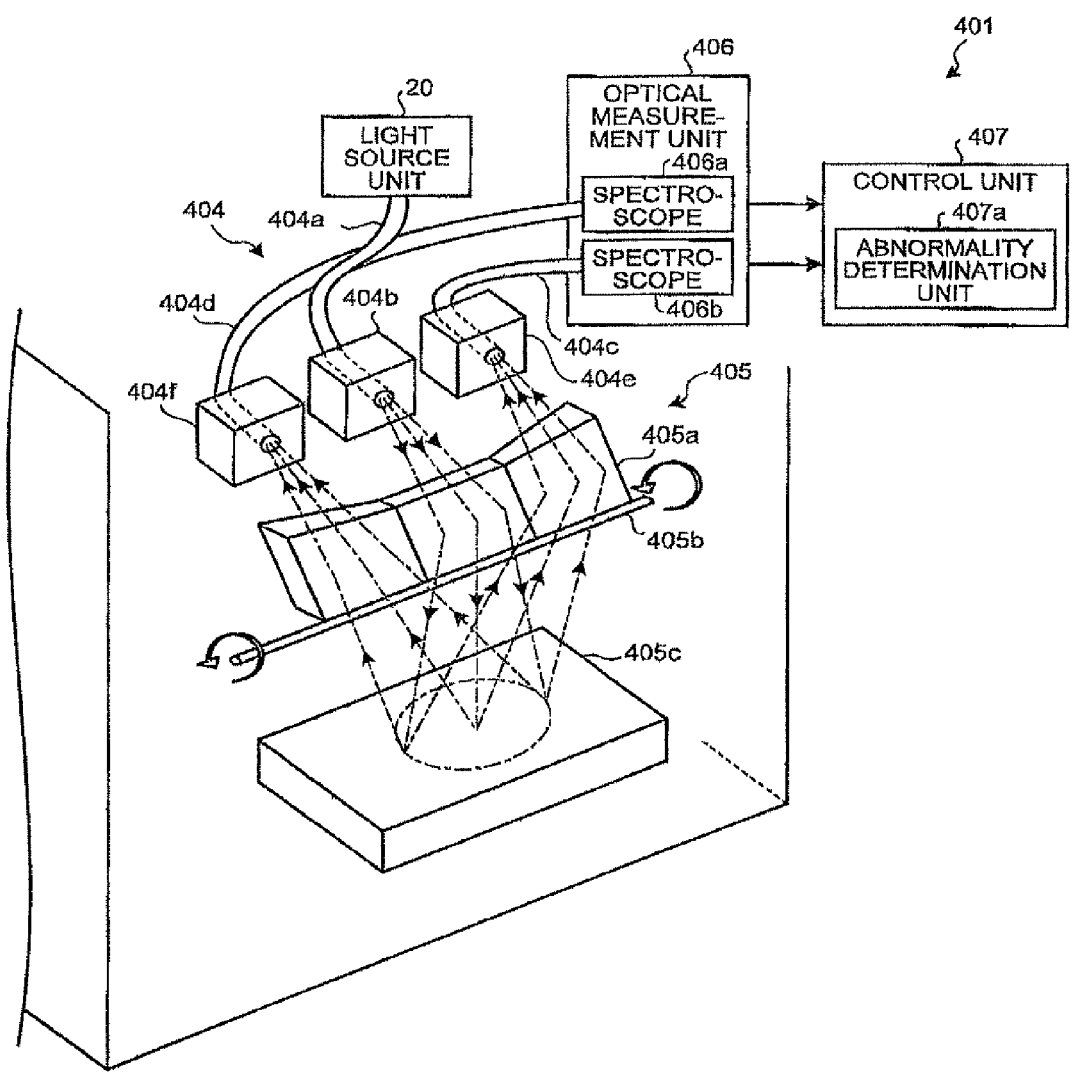
FIG. 16 is a partially cut-away perspective view schematically illustrating the optical measurement system according to the fourth embodiment of the invention.

Next, a fourth embodiment of the invention will be described. FIG. 15 is a schematic diagram illustrating a schematic configuration of the optical measurement system according to the fourth embodiment. FIG. 16 is a partially cut-away perspective view illustrating the optical measurement system according to the fourth embodiment. An optical measurement system 400 illustrated in FIGS. 15 and 16 is applied to an LEBS (low coherence enhanced backscattering spectroscopy) device and the like. In FIGS. 15 and 16, like reference numerals denote like elements as in the configuration of the optical measurement system described in the aforementioned embodiments, and description thereof will not be repeated.

As illustrated in FIGS. 15 and 16, the optical measurement system 400 includes an optical measurement apparatus 401 that performs optical measurement by irradiating illumination light onto tissue and measuring the detection light reflected or scattered by tissue and a measurement probe 402 introduced into a subject.

The optical measurement apparatus 401 includes a power switch 403 that activates the optical measurement apparatus 401, a first optical path 404 that transmits the illumination light emitted by the light source unit 20, an optical path switching unit 405 that switches the optical path of the illumination light, an optical measurement unit 406 that measures detection light, and a control unit 407 that controls the operation of the optical measurement apparatus 401.

The first optical path 404 transmits the illumination light emitted by the light source unit 20 to the optical measurement unit 406. The first optical path 404 includes an illumination optical fiber 404a that transmits the illumination light, an illumination optical fiber support portion 404b that supports the illumination optical fiber 404a, detection optical fibers 404c and 404d that transmits the illumination light or the detection light, and detection optical fiber support portions 404e and 404f that support the detection optical fibers 404c and 404d, respectively.

The optical path switching unit 405 is arranged in the middle of the optical path between the connector 21 and the light source unit 20 or the optical measurement unit 406. The optical path switching unit 405 includes a reflection member 405a arranged movably between the insertion position and the retreating position to reflect the illumination light, a support member 405b that rotatably supports the reflection member 405a, and a calibration member 405c that reflects the illumination light reflected at the reflection member 405a. The reflection surface of the reflection member 405a is integratedly formed with a predetermined angle such that an irradiation region for irradiating the illumination light emitted by the illumination optical fiber 404a onto the calibration member 405c and a measurement region where measurement is performed by each of the spectroscopes 406a and 406b on the calibration member 405c nearly match each other.

The optical measurement unit 406 includes spectroscopes 406a and 406b. The spectroscopes 406a and 406b measure the illumination light or the detection light transmitted by the detection optical fibers 404c and 404d, respectively, and output the result to the control unit 407.

The control unit 407 has an abnormality determination unit 407a. The abnormality determination unit 407a determines whether or not abnormality occurs in the optical measurement apparatus 401 based on the measurement value output by the optical measurement unit 406.

Figure 17:
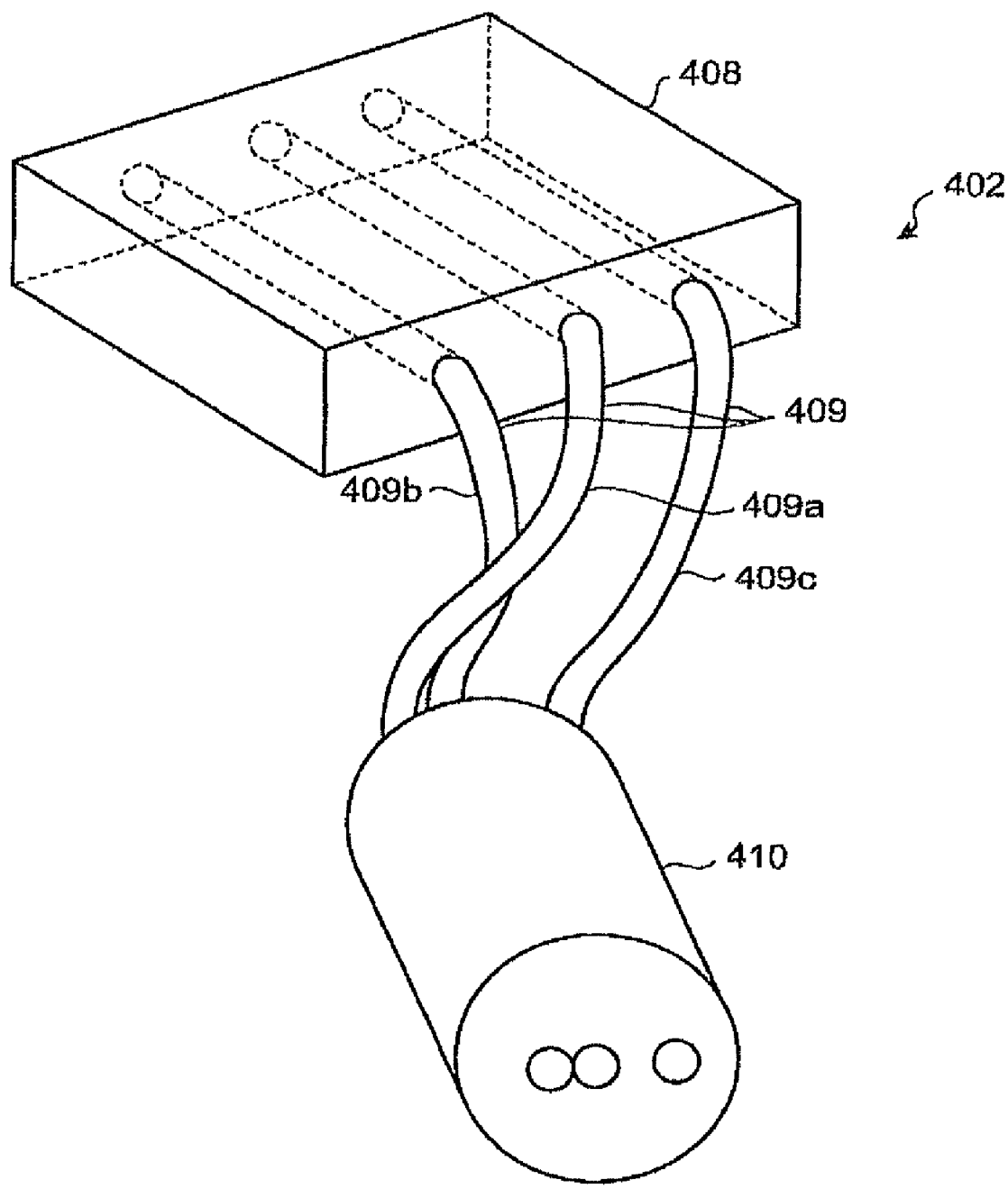
FIG. 17 is a schematic diagram illustrating a schematic configuration of the measurement probe of FIG. 15.

FIG. 17 is a schematic diagram illustrating a schematic configuration of the measurement probe of FIG. 15. As illustrated in FIG. 17, the measurement probe 402 includes a base end portion 408, a flexible portion 409, and a leading end portion 410. The base end portion 408 is detachably connected to the connector 21 of the optical measurement apparatus 401. The flexible portion 409 includes an optical fiber, of which one end is connected to the base end portion 408 and the other end is connected to the leading end portion 410. The flexible portion 409 includes an illumination optical fiber 409a that transmits the illumination light to the leading end portion 410 and detection optical fibers 409b and 409c that transmit, to the spectroscopes 406a and 406b, respectively, the detection light incident from the leading end portion 410. The leading end portion 410 maintains the exposed edge faces of the detection optical fibers 409b and 409c in parallel so that the detection light reflected at the tissue S3 is incident with a certain scattering angle $(\theta_1, \theta_2)$ (refer to FIGS. 17 and 18).

An outline of the process performed by the optical measurement system 400 having the aforementioned configuration will be described. According to the fourth embodiment, abnormality determination for the optical measurement apparatus 401 and the measurement probe 402 is performed similarly to the second embodiment, and only the measurement of tissue S3 is different. For this reason, hereinafter, only the measurement of tissue S3 using the optical measurement system 400 will be described.

Figure 18:
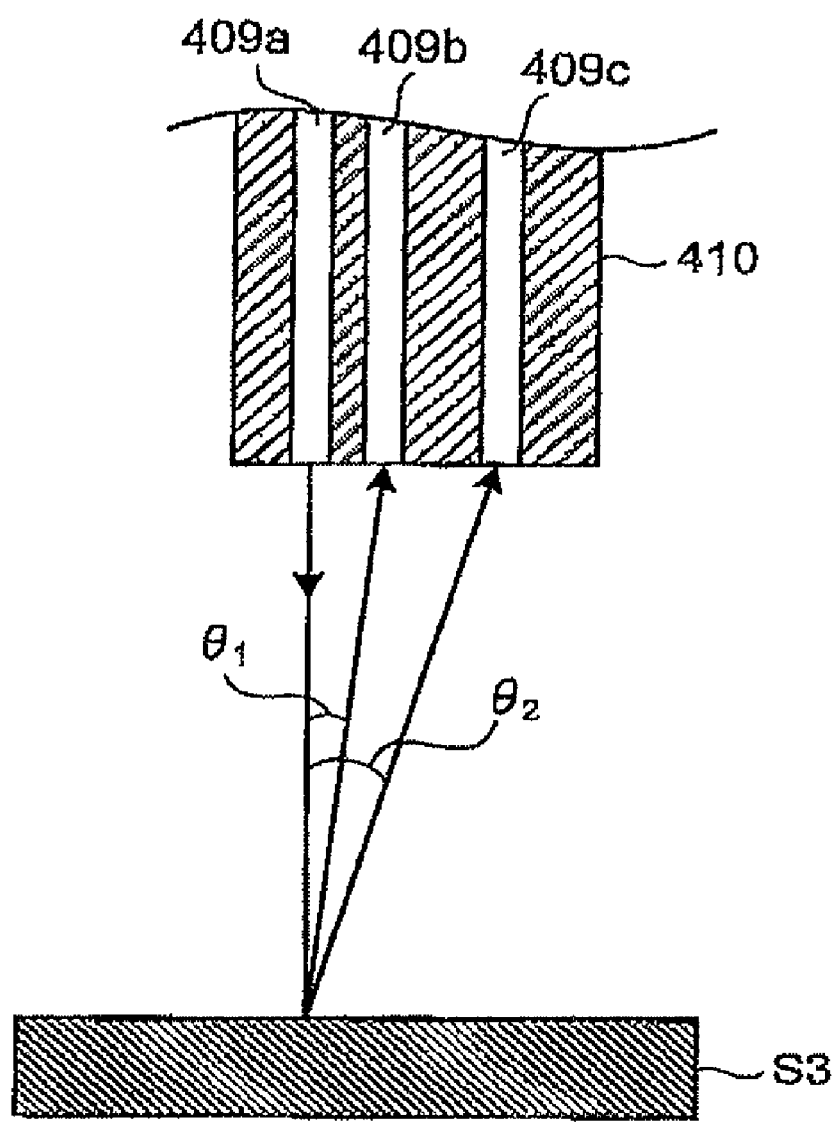
FIG. 18 is an explanatory diagram illustrating a scattering angle at which detection light is incident to the detection optical fiber when illumination light is irradiated onto and reflected by tissue using the measurement probe of FIG. 17.

First, the control unit 407 causes the illumination light of the light source unit 20 to be emitted to the second optical path 25 and causes the illumination light to be irradiated onto tissue 83. In this case, as illustrated in FIG. 18, the illumination light irradiated through the illumination optical fiber 409a is reflected at the tissue S3, is incident to each of the detection optical fibers 409b and 409c provided in the leading end portion 410 at a certain scattering angle, and is measured by the spectroscopes 406a and 406b.

Then, the control unit 407 obtains the measurement value of the detection light measured by each of the spectroscopes 406a and 406b, computes a scattering spectrum of the detection light, and outputs the computation result to the output unit 27. As a result, a user can diagnose whether or not there is a diseased tissue.

In the fourth embodiment described above, the optical path switching unit 405 switches the optical path of the illumination light emitted by the light source unit 20 into the first optical path 404 or the second optical path 25, so that abnormality in the optical measurement apparatus 401 can be recognized similarly to the first embodiment described above. As a result, it is possible to specify an abnormal portion even when abnormality occurs in the optical measurement apparatus 401 or the measurement probe 402.

Fifth Embodiment

Figure 19:
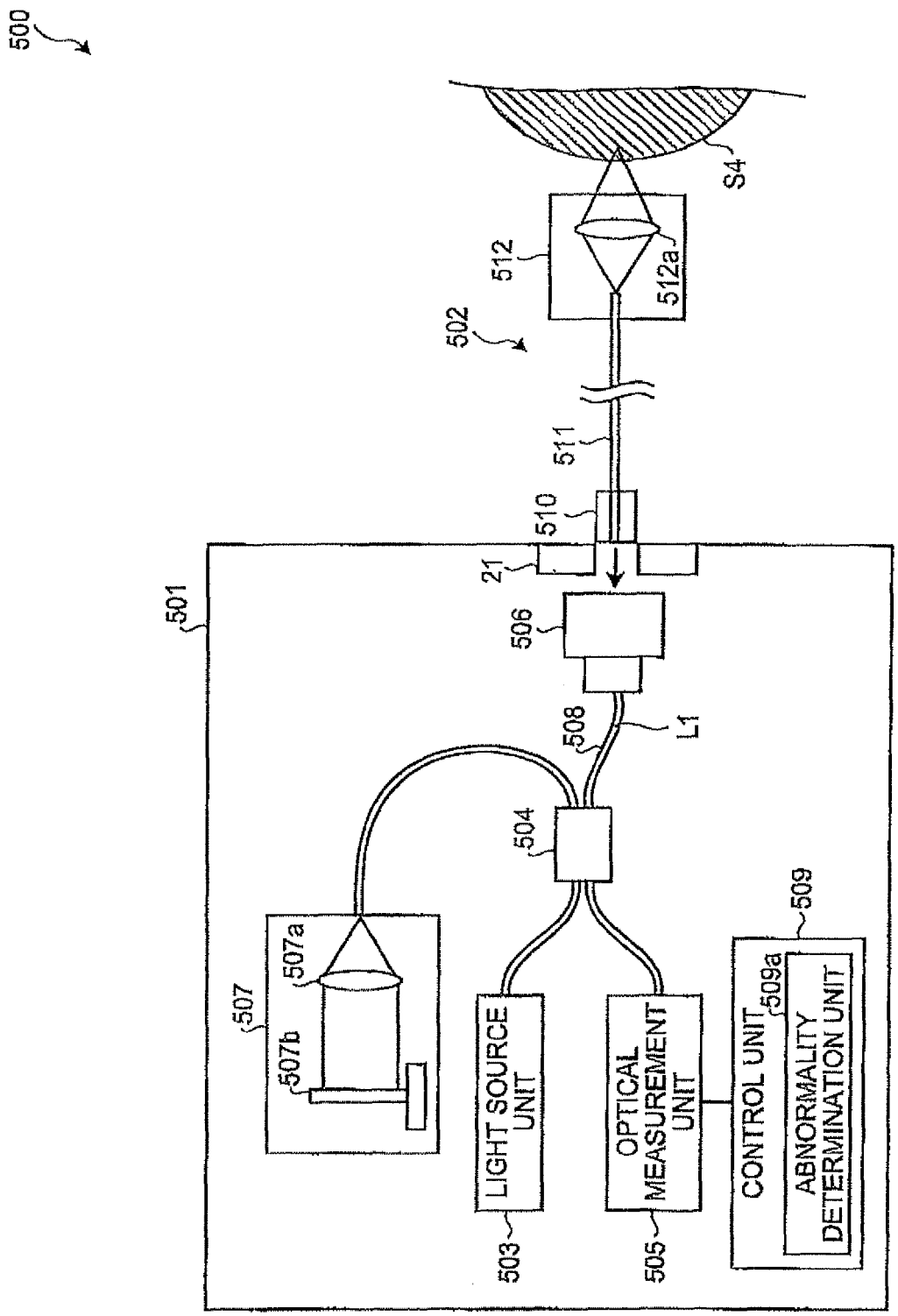
FIG. 19 is a schematic diagram illustrating a schematic configuration of the optical measurement system according to a fifth embodiment of the invention.
Figure 20:
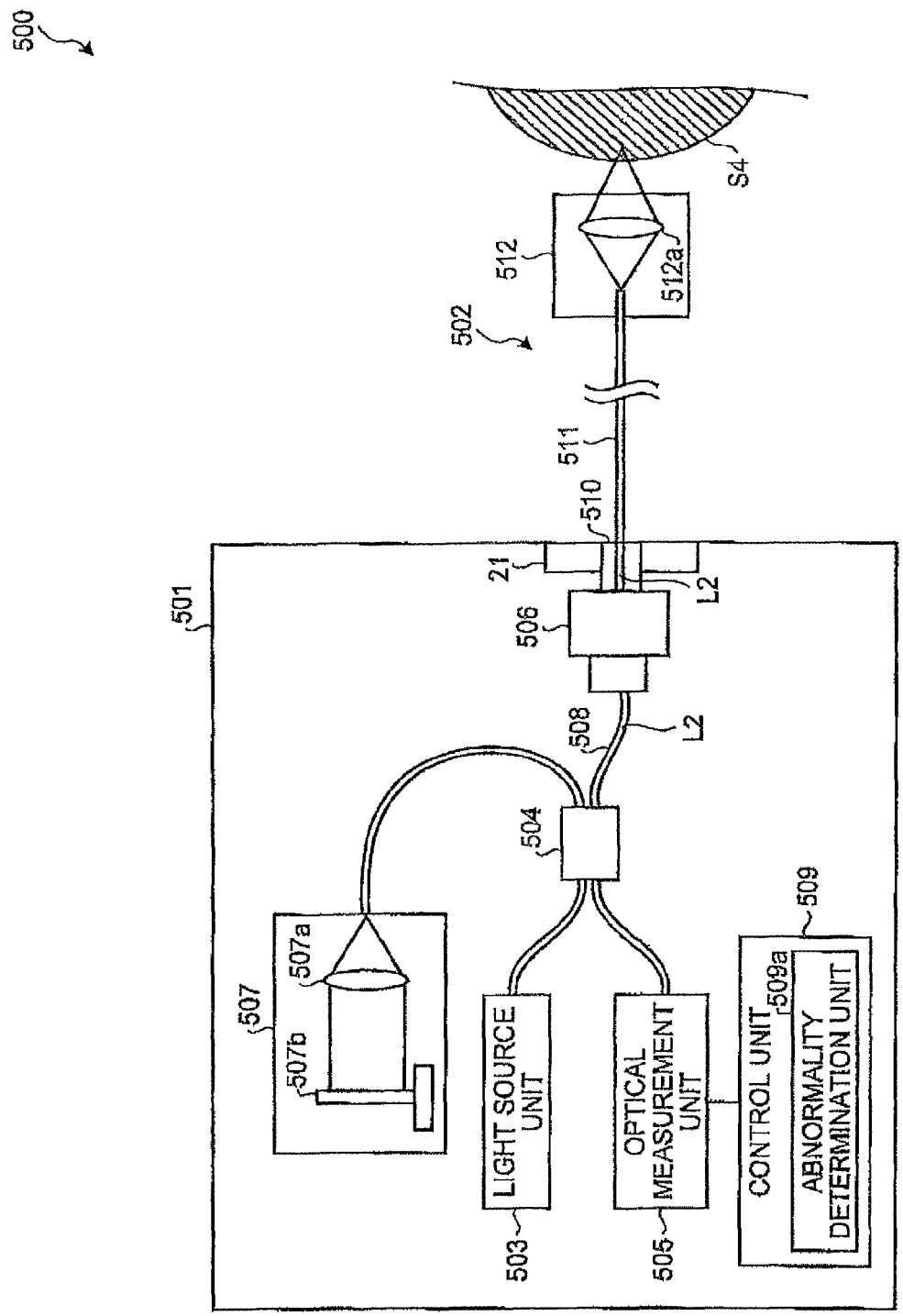
FIG. 20 is a schematic diagram illustrating a schematic configuration of the optical measurement system according to the fifth embodiment of the invention.

Next, a fifth embodiment of the invention will be described. FIGS. 19 and 20 are schematic diagrams illustrating a schematic configuration of the optical measurement system according to the fifth embodiment. An optical measurement system 500 illustrated in FIGS. 19 and 20 is applied to an OCT (optical coherence tomography) device, a confocal endoscope device, and the like. In addition, in FIGS. 19 and 20, like reference numerals denote like elements as in the configuration of the optical measurement system described in the aforementioned embodiments, and description thereof will not be repeated.

As illustrated in FIGS. 19 and 20, the optical measurement system 500 includes an optical measurement apparatus 501 and a measurement probe 502.

The optical measurement apparatus 501 includes a light source unit 503 that irradiates the illumination light onto the tissue S4 through the measurement probe 502, an optical branching unit 504 that branches the illumination light emitted by the light source unit 503, an optical measurement unit 505 that measures the illumination light or the detection light transmitted through the measurement probe 502 and the optical branching unit 504, an optical path switching unit 506 that switches the illumination light emitted by the light source unit 503, a reference mirror unit 507 that reflects the illumination light transmitted through the optical branching unit 504, a first optical path 508 that transmits the illumination light to the measurement probe 502 through the optical branching unit 504, and a control unit 509 that controls the operation of the optical measurement apparatus 501.

The light source unit 503 includes a laser light source such as an SLD (super luminescent diode) for emitting a low coherent light and a single or a plurality of lenses. The light source unit 503 emits the illumination light to the tissue S4 through the optical branching unit 504 and the measurement probe 502.

The optical branching unit 504 includes a fiber coupler. The optical branching unit 504 branches the illumination light emitted from the light source unit 503 into the reference mirror unit 507 and the measurement probe 502. The optical branching unit 504 transmits the detection light incident through the measurement probe 502 to the optical measurement unit 505.

The optical measurement unit 505 measures interference light generated when the optical path length of the reference mirror unit 507 matches the optical path length of the measurement probe 502. The optical measurement unit 505 outputs the measurement value of the measured interference light to the control unit 509.

Figure 21:
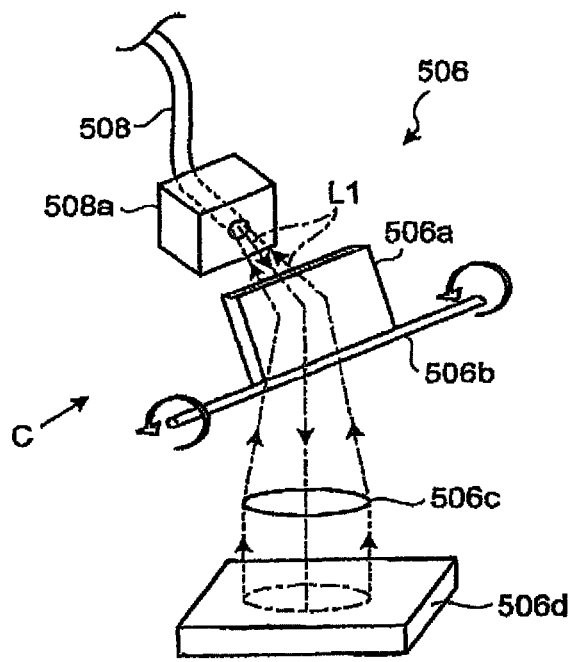
FIG. 21 is a perspective view schematically illustrating a schematic configuration of the optical path switching unit of FIG. 20.
Figure 22:
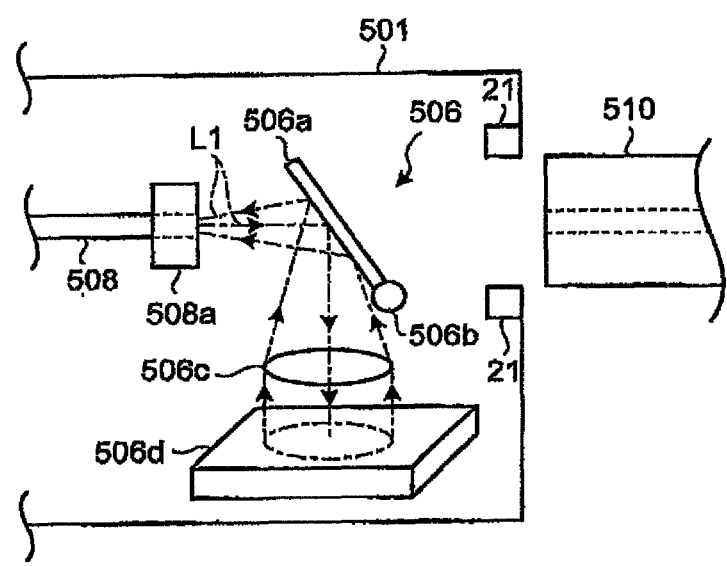
FIG. 22 is a cross-sectional view schematically illustrating a cross section as seen from an arrow C of FIG. 21.

FIG. 21 is a perspective view schematically illustrating a schematic configuration of the optical path switching unit 506. FIG. 22 is a cross-sectional view schematically illustrating a cross section as seen from the arrow C of FIG. 21. As illustrated in FIGS. 21 and 22, the optical path switching unit 506 includes a reflection member 506a, a rotation support member 506b, and a lens 506c, and a calibration member 506d. The reflection member 506a is arranged movably between the insertion position and the retreating position to reflect the illumination light to the lens 506c. The rotation support member 506b rotatably supports the reflection member 506a. The lens 506c collimates the illumination light reflected by the reflection member 506a or condenses the illumination light reflected by the calibration member 506d. The calibration member 506d reflects, to the reflection member 506a, the illumination light incident through the lens 506c.

The reference mirror unit 507 includes a condensing lens 507a and a mirror portion 507b. The reference mirror unit 507 reflects, to the optical measurement unit 505, the illumination light transmitted through the optical branching unit 504. In addition, the reference mirror unit 507 may be provided with a driving unit for driving the mirror portion 507b to a scanning direction so as to change the optical path length of the reference mirror unit 507.

The first optical path 508 includes an optical fiber. One end of the first optical path 508 is connected to the optical branching unit 504, and the other end is connected to the measurement probe 502. The first optical path 508 is supported by a support member 508a.

The control unit 509 transfers instructions or data for each unit of the optical measurement apparatus 501 to collectively control the operation of the optical measurement apparatus 501. The control unit 509 has an abnormality determination unit 509a. The abnormality determination unit 509a determines whether or not abnormality occurs in the optical measurement apparatus 501 and the measurement probe 502 based on the measurement value output by the optical measurement unit 505.

The measurement probe 502 irradiates the illumination light emitted by the light source unit 503 onto the tissue 54 and transmits the detection light reflected at the tissue S4 to the optical measurement unit 505. The measurement probe 502 has a base end portion 510, a flexible portion 511, and a leading end portion 512. The base end portion 510 is connected to the connector 21 of the optical measurement apparatus 501. The flexible portion 511 includes an optical fiber, of which one end is connected to the base end portion 510, and the other end is connected to the leading end portion 512. The leading end portion 512 has a condensing lens 512a. The leading end portion 512 condenses the illumination light transmitted from the flexible portion 511 using the condensing lens 512a to irradiate it onto the tissue S4, and condenses the detection light obtained by reflecting the illumination light at the tissue 54 using the condensing lens 512a to transmit it to the optical measurement unit 505.

The optical measurement system 500 having such a configuration further includes a first optical path L1 and a second optical path L2.

The first optical path L1 transmits the illumination light emitted by the light source unit 503 to the optical path switching unit 506 through the optical branching unit 504 and the first optical path 508 and transmits the illumination light reflected at the optical path switching unit 506 to the optical measurement unit 505 through the first optical path 508 and the optical branching unit 504 (refer to FIG. 19).

The second optical path L2 transmits the illumination light emitted by the light source unit 503 to the tissue S4 through the optical branching unit 504, the first optical path 508, and the measurement probe 502, and transmits the detection light obtained by reflecting the illumination light at the tissue S4 to the optical measurement unit 505 through the measurement probe 502, the first optical path 508, and the optical branching unit 504 (refer to FIG. 20).

Next, a manipulation sequence of the optical measurement system 500 will be described. FIGS. 23A, 23B, 24A and 24B are explanatory diagrams illustrating the operation of the optical path switching unit 506. First, before the measurement probe 502 is connected to the optical measurement apparatus 501 (refer to FIGS. 23A and 24A), the optical path switching unit 506 switches the optical path of the illumination light into the first optical path L1, and the light source unit 503 emits the illumination light to the first optical path L1.

Subsequently, the optical measurement unit 505 measures the illumination light transmitted through the first optical path L1 and outputs the measurement value to the control unit 509.

Then, the abnormality determination unit 509a determines whether or not abnormality occurs in the optical measurement apparatus 501 based on the measurement value output by the optical measurement unit 505. In this case, the abnormality determination unit 509a may output, to the output unit (not illustrated), information indicating that abnormality occurs in the optical measurement apparatus 501.

Figure 23A:
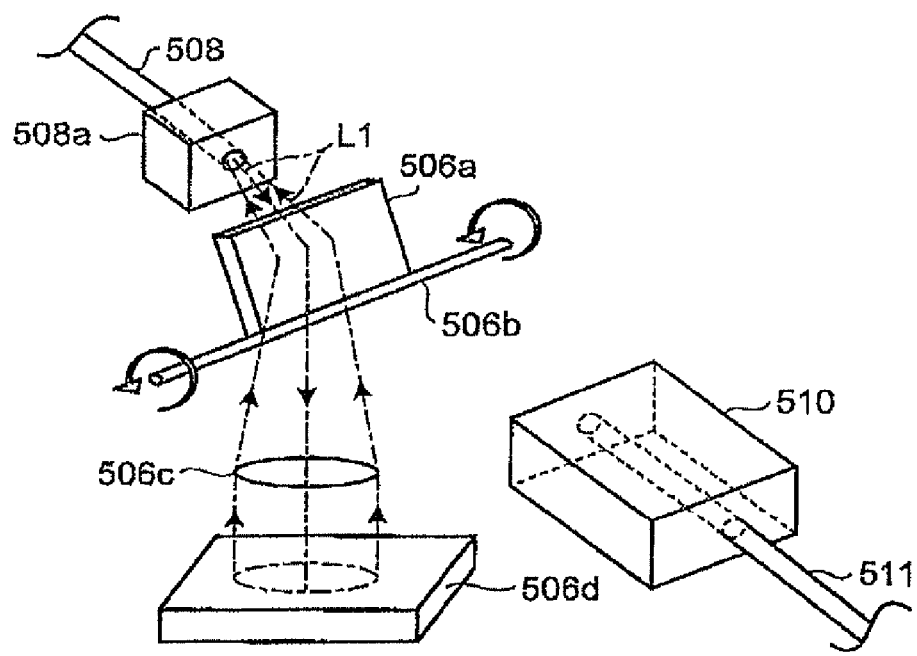
FIGS. 23A and 23B are explanatory diagrams illustrating the operation of the optical path switching unit of FIG. 20.
Figure 23B:
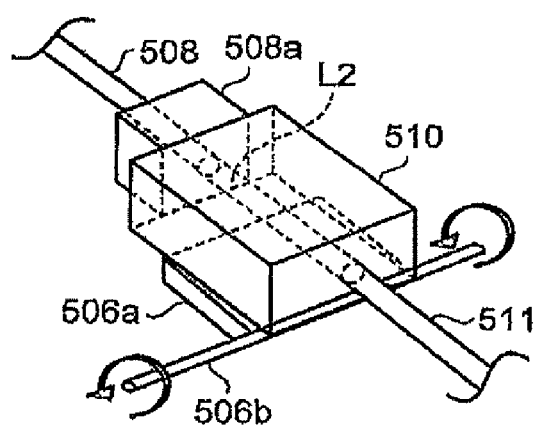
Figure 24A:
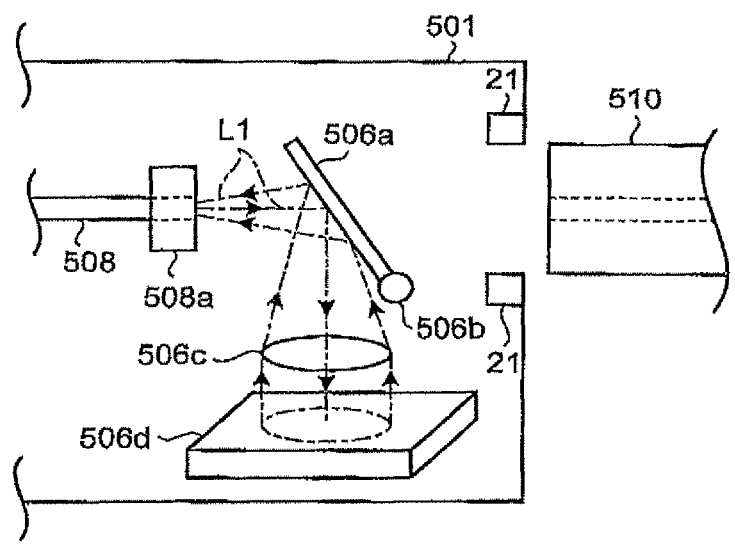
FIGS. 24A and 24B are explanatory diagrams illustrating the operation of the optical path switching unit of FIG. 20.
Figure 24B:
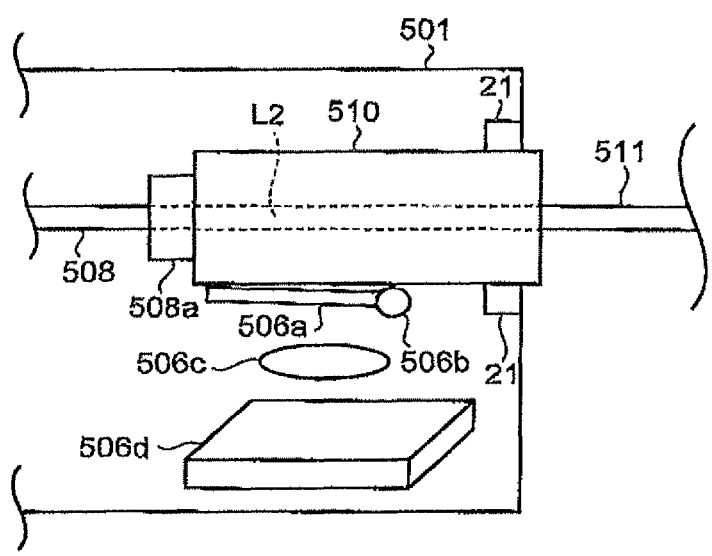

After it is determined that the condition of the optical measurement apparatus 501 is normal, the optical path is switched to the second optical path L2 by connecting the measurement probe 502 to the optical measurement apparatus 501 (refer to FIGS. 23B and 24B). After the cap portion 40 (refer to FIG. 3) is connected to the leading end portion 512 of the measurement probe 502, the abnormality determination unit 509a determines whether or not abnormality occurs in the measurement probe 502. In this case, the abnormality determination unit 509a may output, to the output unit (not illustrated), information indicating that abnormality occurs in the measurement probe 502.

After it is determined that the condition of the measurement probe 502 is normal, a user starts measurement of the tissue S4 using the optical measurement system 500.

In the fifth embodiment described above, the optical path switching unit 506 switches the optical path of the illumination light emitted by the light source unit 503 into the first optical path L1 or the second optical path L2 so that abnormality in the optical measurement apparatus 501 can be recognized similarly to the first embodiment described above. As a result, it is possible to easily specify an abnormal portion even when abnormality occurs in the optical measurement apparatus 501 or the measurement probe 502.

First Modification of Fifth Embodiment

Figure 25:
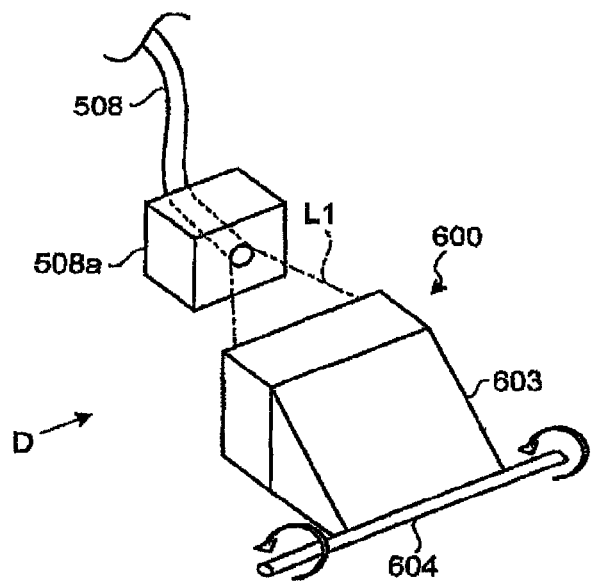
FIG. 25 is a perspective view schematically illustrating a schematic configuration of the optical path switching unit according to a modification of the fifth embodiment of the invention.
Figure 26:
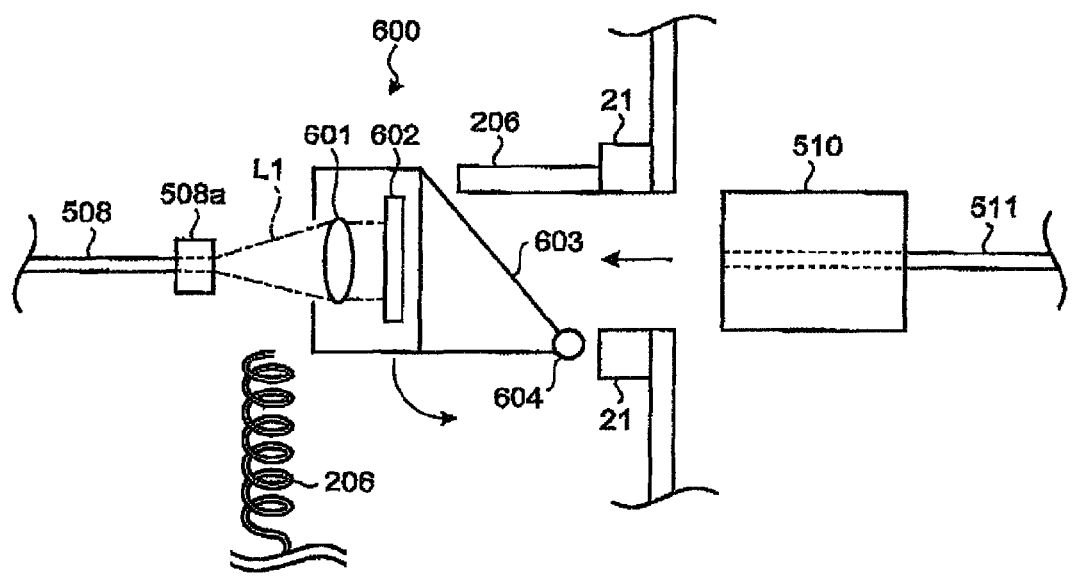
FIG. 26 is a cross-sectional view schematically illustrating a cross section as seen from an arrow D of FIG. 25.

A first modification of the fifth embodiment will be described with reference to FIG. 25. FIG. 25 is a perspective view schematically illustrating an optical path switching unit 600 according to the first modification of the fifth embodiment. FIG. 26 is a schematic diagram schematically illustrating a cross section as seen from the arrow D of FIG. 25.

As illustrated in FIGS. 25 and 26, the optical path switching unit 600 is arranged movably between the insertion position and the retreating position and reflects the illumination light emitted by the light source unit 503. The optical path switching unit 600 includes a lens 601 that collimates or condenses the illumination light, a reflection member 602 that reflects the illumination light irradiated through the lens 601, a support member 603 that supports the lens 601 and the reflection member 602, and a rotating portion 604 that rotatably supports the support member 603.

In the first modification of the fifth embodiment described above, similar to the fifth embodiment, the optical path switching unit 600 switches the optical path of the illumination light emitted from the light source unit 503 into the first optical path L1 until the measurement probe 502 is connected to the optical measurement apparatus 501. Therefore, it is possible to recognize abnormality in the optical measurement apparatus 501 as power is supplied to the optical measurement apparatus 501.

Second Modification of Fifth Embodiment

Figure 27:
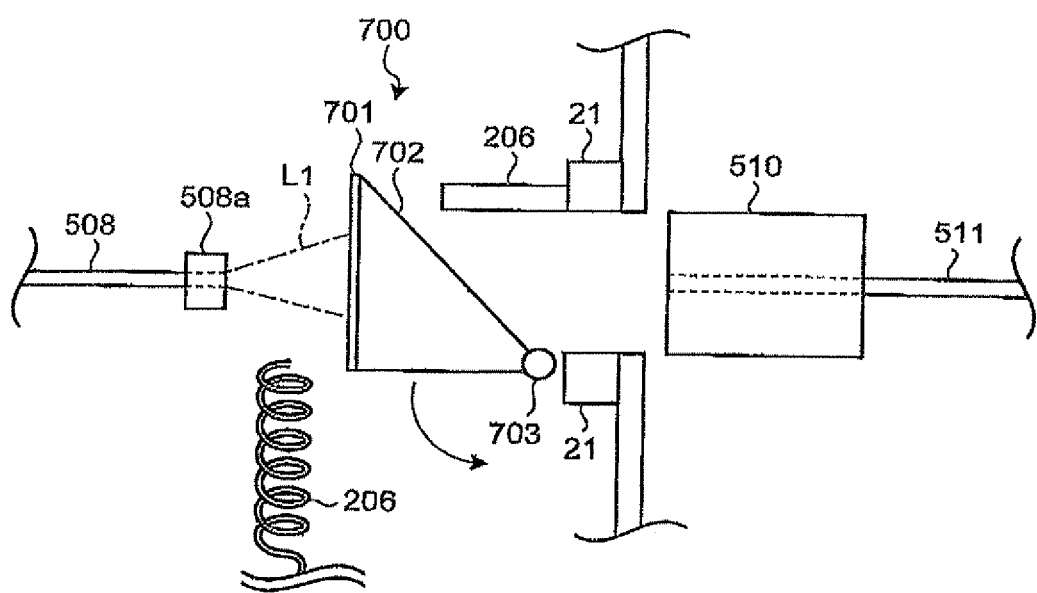
FIG. 27 is a perspective view schematically illustrating a schematic configuration of the optical path switching unit according to a modification of the fifth embodiment of the invention.

A second modification of the fifth embodiment will be described with reference to FIG. 27. FIG. 27 is a schematic diagram schematically illustrating a cross section of an optical path switching unit 700 according to the second modification of the fifth embodiment.

As illustrated in FIG. 27, the optical path switching unit 700 is arranged movably between the insertion position and the retreating position to diffuse the illumination light emitted by the light source unit 503. The optical path switching unit 700 includes a diffusing member 701 that diffuses the illumination light irradiated from the first optical path 508, a diffusing support member 702 that supports the diffusing member 701, and a rotating portion 703 that rotatably supports the diffusing support member 702.

In the second modification according to the fifth embodiment described above, similar to the fifth embodiment described above, the optical path switching unit 700 switches the optical path of the illumination light emitted from the light source unit 503 into the first optical path L1 until the measurement probe 502 is connected to the optical measurement apparatus 501. Therefore, it is possible to recognize abnormality in the optical measurement apparatus 501 as power is supplied to the optical measurement apparatus 501.

Reference Example

In the optical measurement system according to the first to fifth embodiments described above, in order to guarantee analysis accuracy of the analysis result, it is necessary to perform a calibration process before the measurement of tissue starts. However, since the calibration process depends on a user, the measurement of tissue may start without performing the calibration process. In this regard, the reference example of the embodiment provides an optical measurement system capable of reliably executing the calibration process of the optical measurement system before the measurement of tissue is performed.

Figure 28:
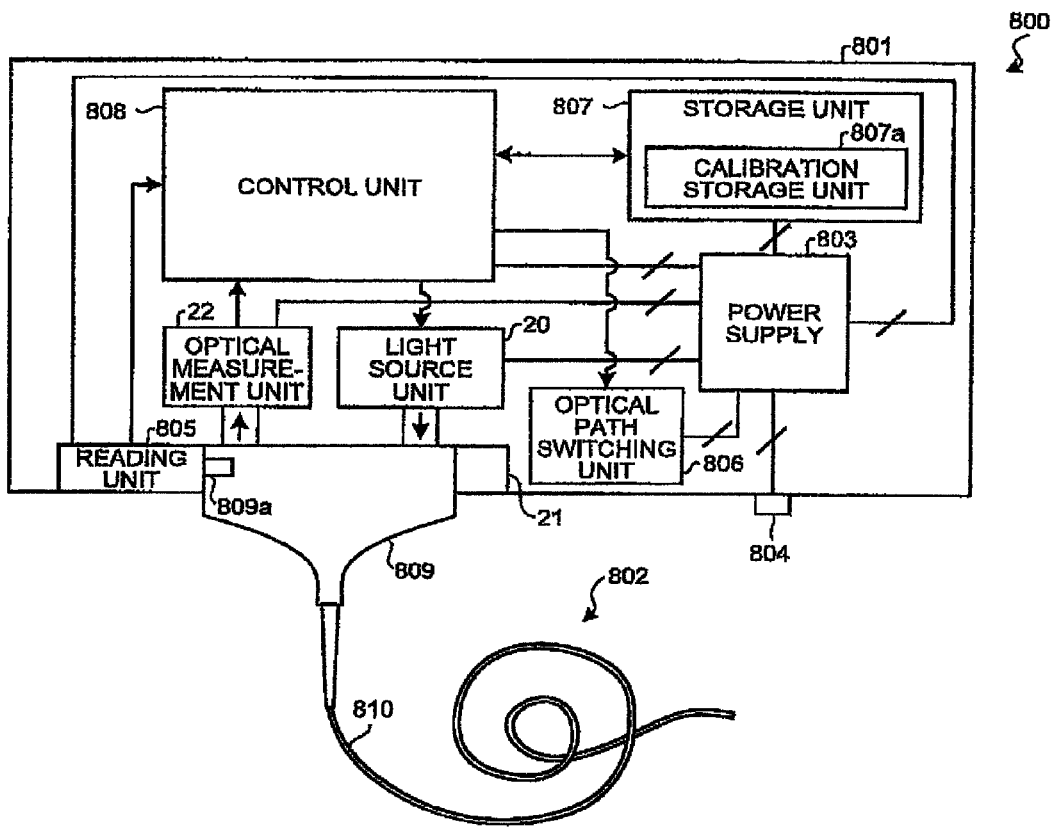
FIG. 28 is a schematic diagram illustrating a schematic configuration of the optical measurement system as a reference example according to the first to fifth embodiments.

FIG. 28 is a schematic diagram illustrating a schematic configuration of an optical measurement system 800 in the reference example according to the embodiment of the invention. In FIG. 28, like reference numerals denote like elements as in the configuration of the optical measurement system described in the aforementioned embodiments, and description thereof will not be repeated.

As illustrated in FIG. 28, an optical measurement system 800 includes an optical measurement apparatus 801 that irradiates the illumination light onto tissue and measures the detection light reflected at the tissue and a measurement probe 802 introduced into a subject.

The optical measurement apparatus 801 includes a power supply 803 that supplies power to each unit of the optical measurement apparatus 801, a switch unit 804 that activates the power supply 803, a reading unit 805 that reads various types of information, an optical path switching unit 806 that switches the optical path of the illumination light emitted by the light source unit 20, a storage unit 807 that stores various types of information on the optical measurement apparatus 801, and a control unit 808 that controls the operation of the optical measurement apparatus 801.

The reading unit 805 includes an RFID reader. The reading unit 805 reads a radio IC tag such as an RFID tag and outputs the read information to the control unit 808.

Figure 29:
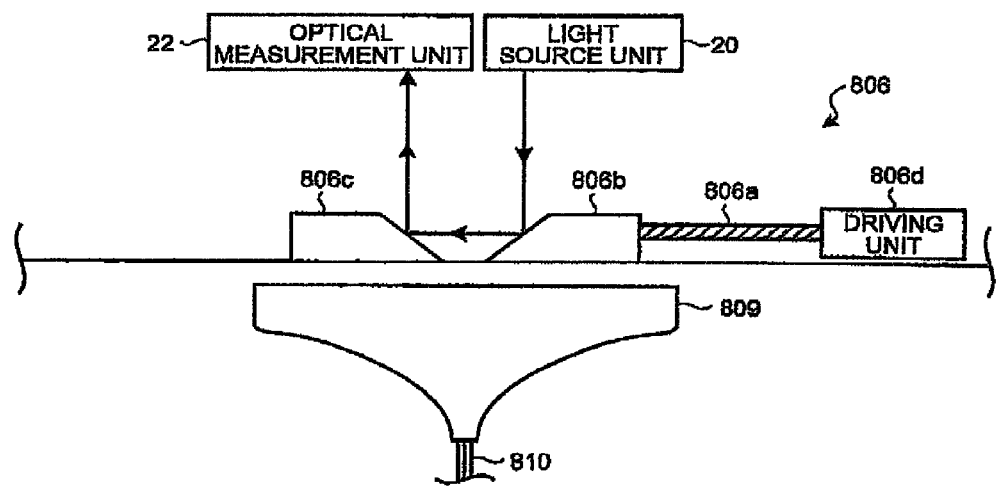
FIG. 29 is a schematic diagram illustrating a schematic configuration of the optical path switching unit of FIG. 28.

FIG. 29 is a schematic diagram illustrating a schematic configuration of the optical path switching unit 806. As illustrated in FIG. 29, an optical path switching unit 806 includes a piston portion 806a that can forwardly and backwardly move in a direction perpendicular to the optical path of the illumination light emitted by the light source unit 20, a first reflection member 806b provided in the leading end of the piston portion 806a to reflect the illumination light at a predetermined angle, a second reflection member 806c provided in the leading end of the piston portion 806a to reflect the illumination light reflected at the first reflection member 806b to the optical measurement unit 22, and a driving unit 806d that drives the piston portion 806a.

A storage unit 807 has a calibration storage unit 807a. The calibration storage unit 807a stores the measurement value of the calibration process of the optical measurement apparatus 801 performed in the shipment of the optical measurement apparatus 801. Specifically, the calibration storage unit 807a stores, as the calibration information, the detection light intensity ($M_e$) of the illumination light measured in a manufacturing factory where the optical measurement apparatus 801 is manufactured. This detection light intensity ($M_a$) is obtained, for example, such that the light source unit 20 emits the illumination light, and the optical measurement unit 22 measures the illumination light incident through the first and second reflection members 806b and 806c under the condition of FIG. 29.

The measurement probe 802 includes an illumination optical fiber that emits the illumination light to tissue and a plurality of detection optical fibers where the detection light reflected at the tissue is incident at a different angle. The measurement probe 802 has a base end portion 809 and a flexible portion 810. The base end portion 809 is detachably connected to the connector 21 of the optical measurement apparatus 801. The flexible portion 810 has flexibility. The flexible portion 810 transmits the illumination light emitted from the light source unit 20 to the leading end where the edge face of the optical fiber is exposed, and transmits the detection light incident through the leading end to the optical measurement unit 22. In addition, the base end portion 809 has a storage medium 809a for storing unique information of the measurement probe 802.

Here, the unique information is a criterion reference light intensity ($I_{ws}$) measured by executing the calibration process using the optical measurement apparatus 801, the measurement probe 802, and the calibration member in a manufacturing factory where the measurement probe 802 is manufactured. In addition, the unique information may include various types of information such as a type of the measurement probe 802, a manufacturing date, and an ID code.

A computation method of tissue using the optical measurement system 800 having the aforementioned configuration will be described. Typically, the following condition is satisfied:

$$I_n = I_s/I_w,$$

where $I_n$ denotes a computation result (standardized light intensity) of tissue computed using the optical measurement system 800, $I_s$ denotes a detection light intensity obtained by measuring the detection light reflected from tissue, and $I_w$ denotes a reference light intensity obtained by measuring the detection light reflected from the calibration member.

However, in the optical measurement apparatus 801, since the optical characteristic of the optical measurement apparatus 801 temporally changes due to aging of the light source unit 20, a minute deviation of an optical system, or the like, the reference light intensity ($I_w$) changes. Meanwhile, since the measurement probe 802 is a disposable type, the optical characteristic of the measurement probe 802 does not change.

In this regard, it is necessary to perform calibration for the reference light intensity. Specifically, the following condition is satisfied:

$$I_w = I_{ws} \times M/M_s,$$

Where M denotes a detection light intensity obtained when the light source unit 20 emits the illumination light under the condition of FIG. 29, and the optical measurement unit 22 measures the illumination light incident through the first and second reflection members 806b and 806c, $I_{ws}$ denotes a criterion reference light intensity included in the unique information read by the reading unit 805, and $M_s$ denotes a detection intensity stored by the calibration storage unit 807a of the storage unit 807.

In this manner, in the control unit 808, the reading unit 805 obtains the criterion reference light intensity ($I_{ws}$) and the detection intensity ($M_s$) stored in the calibration storage unit 807a from the storage medium 809a attached to the base end portion 809 when the measurement probe 802 is connected to the optical measurement apparatus 801, and the reference light intensity ($I_w$) is calibrated. Therefore, it is not necessary to separately perform the calibration process using the calibration member.

In the reference example of the embodiments described above, the detection intensity ($M_s$) is stored in the calibration storage unit 807a, and the storage medium 809a for storing unique information including the reference light intensity ($I_{ws}$) is attached to the base end portion 809 of the measurement probe 802. Therefore, even when the configurations of the optical measurement apparatus 801 and the measurement probe 802 are different, it is possible to reliably perform standardization of the detection light intensity of tissue without performing the calibration process using the calibration member. As a result, it is possible to reliably preventing a user from forgetting execution of the calibration process.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus comprising:
   a connector where a base end portion of a measurement probe introduced into a subject is connected;
   a light source unit that emits illumination light irradiated from a leading end of the measurement probe;
   an optical measurement unit that measures reflection light and/or scattering light of the illumination light incident through the measurement probe;
   a first optical path that transmits the illumination light emitted by the light source unit to the optical measurement unit;
   a second optical path that transmits, to the measurement probe, the illumination light emitted by the light source unit and transmits, to the optical measurement unit, reflection light and/or scattering light of the illumination light incident through the measurement probe; and
   an optical path switching unit that switches an optical path for transmitting the illumination light into the first optical path or the second optical path.

2. The optical measurement apparatus according to claim 1, wherein the optical path switching unit switches an optical path for transmitting the illumination light into the second optical path when the measurement probe is connected to the connector, and switches the optical path for transmitting the illumination light into the first optical path when the measurement probe is not connected from the connector.

3. The optical measurement apparatus according to claim 2, further comprising:
   an input unit that receives an instruction signal for instructing switching of the optical path using the optical path switching unit; and
   a control unit that drives the optical path switching unit so as to switch the optical path for transmitting the illumination light into the first optical path or the second optical path depending on the instruction signal input to the input unit.

4. The optical measurement apparatus according to claim 2, further comprising:
   a probe detection unit that detects whether or not the measurement probe is installed in the connector; and
   an optical path change unit that drives the optical path switching unit so as to change the optical path for transmitting the illumination light to the first optical path or the second optical path depending on a detection result of the probe detection unit.

5. The optical measurement apparatus according to claim 4, further comprising:
   a storage unit that stores first threshold value information indicating a measurement value of illumination light measured by the optical measurement unit when the first optical path is normal and second threshold value information indicating a measurement value of illumination light measured by the optical measurement unit when the second optical path is normal;
   a threshold value selection unit that selects the first threshold value information or the second threshold value information stored in the storage unit depending on the optical path changed by the optical path change unit; and
   an abnormality determination unit that determines whether or not abnormality occurs in the first optical path or the second optical path based on the optical path changed by the optical path change unit and a selection result of the threshold value selection unit.

6. The optical measurement apparatus according to claim 5, further comprising an output unit that outputs information indicating that abnormality occurs in the first or second optical path when the abnormality determination unit determines that abnormality occurs in the first or second optical path.

7. The optical measurement apparatus according to claim 2, wherein the optical switching unit has a reflection member movable between an insertion position for insertion in the middle of an optical path between the connector and the light source unit or the optical measurement unit and a retreating position for retreating from the optical path between the connector and the light source unit or the optical measurement unit, and
   the reflection member moves to the retreating position when the measurement probe is connected to the connector and moves to the insertion position when the measurement probe is not connected to the connector.

8. An optical measurement system comprising:
   the optical measurement apparatus according to claim 1;
   wherein the measurement probe is configured to be attached to or detached from the optical measurement apparatus.

9. The optical measurement system according to claim 8, further comprising a calibration module having a calibration member which is detachably provided at a leading end portion of the measurement probe and which serves as an irradiation target of the illumination light when calibration processes of the optical measurement apparatus and the measurement probe are performed.

* * * * *